(12) United States Patent
Gaserod et al.

(10) Patent No.: US 7,671,101 B2
(45) Date of Patent: *Mar. 2, 2010

(54) GELLED BIOPOLYMER BASED FOAM

(75) Inventors: Olav Gaserod, Steinberg (NO); Peder Oscar Andersen, Olso (NO); Rolf Myrvold, Heggedal (NO)

(73) Assignee: FMC Biopolymer AS, Sandvika (NO)

( * ) Notice: Subject to any disclaimer, the term of this patent is extended or adjusted under 35 U.S.C. 154(b) by 0 days.

This patent is subject to a terminal disclaimer.

(21) Appl. No.: 11/592,554

(22) Filed: Nov. 3, 2006

(65) Prior Publication Data

US 2007/0054043 A1    Mar. 8, 2007

Related U.S. Application Data

(62) Division of application No. 10/933,169, filed on Sep. 2, 2004.

(60) Provisional application No. 60/584,357, filed on Jun. 30, 2004, provisional application No. 60/545,700, filed on Feb. 18, 2004, provisional application No. 60/510,063, filed on Oct. 9, 2003, provisional application No. 60/501,500, filed on Sep. 8, 2003.

(51) Int. Cl.
*A61K 9/14* (2006.01)

(52) U.S. Cl. .............. 521/63; 521/64; 521/92; 521/102; 521/123; 424/443; 424/444; 424/445; 424/484

(58) Field of Classification Search ............ 521/63, 521/64, 92, 102, 123; 424/443, 444, 445, 424/484
See application file for complete search history.

(56) References Cited

U.S. PATENT DOCUMENTS

| | | | |
|---|---|---|---|
| 4,948,575 A | 8/1990 | Cole et al. | |
| 5,674,524 A | 10/1997 | Scherr | |
| 5,709,934 A | 1/1998 | Bell et al. | |
| 5,718,916 A | 2/1998 | Scherr | |
| 5,840,777 A | 11/1998 | Eagles et al. | |
| 5,851,461 A | 12/1998 | Bakis et al. | |
| 5,891,558 A | 4/1999 | Bell et al. | |
| 6,080,420 A | 6/2000 | Qin et al. | |
| 6,090,401 A | 7/2000 | Gowan, Jr. et al. | |
| 6,153,292 A | 11/2000 | Bell et al. | |
| 6,201,164 B1 | 3/2001 | Wulff et al. | |
| 6,203,845 B1 | 3/2001 | Qin et al. | |
| 6,251,424 B1 | 6/2001 | Al-Lamee et al. | |
| 6,258,995 B1 | 7/2001 | Gilding et al. | |
| 6,334,968 B1 | 1/2002 | Shapiro et al. | |
| 6,425,918 B1 | 7/2002 | Shapiro et al. | |
| 6,444,199 B1 | 9/2002 | Renn | |
| 6,534,083 B2 | 3/2003 | Gilding et al. | |
| 6,565,878 B2 | 5/2003 | Schoenfeldt et al. | |
| 6,589,328 B1 | 7/2003 | Nussinovitch | |
| 6,656,974 B1 | 12/2003 | Renn et al. | |
| 6,677,318 B1 | 1/2004 | Beisel | |
| 6,696,077 B2 | 2/2004 | Scherr | |
| 7,128,929 B1 | 10/2006 | Scherr | |
| 2003/0072804 A1 | 4/2003 | Hird et al. | |
| 2003/0091610 A1 | 5/2003 | Hird et al. | |
| 2003/0180242 A1 | 9/2003 | Eccard et al. | |
| 2003/0224022 A1 | 12/2003 | Nussinovitch | |
| 2004/0091450 A1 | 5/2004 | Hird et al. | |

FOREIGN PATENT DOCUMENTS

| | | |
|---|---|---|
| GB | 2357765 | 7/2001 |
| JP | S49-119962 | 11/1974 |
| JP | 2004-008539 | 1/2004 |
| JP | 2004-033016 | 2/2004 |
| JP | 2004-236534 | 8/2004 |
| WO | WO 94/17137 | 8/1994 |
| WO | WO 00/19979 | 4/2000 |
| WO | WO 03/037300 | 5/2003 |
| WO | WO 03/092754 | 11/2003 |

OTHER PUBLICATIONS

International Search Report, PCT/IB2004/002849; Jan. 2004.

*Primary Examiner*—Irina S Zemel

(57) ABSTRACT

Gelled biopolymer based foams are disclosed. The gelled foams comprise a cross-linked biopolymer, preferably alginate; optionally, a foaming agent such as hydroxy propyl methyl cellulose; and a plasticizer, preferably glycerin sorbitol, or a mixture thereof, that forms the predominant portion of the gelled foam. The foams are soft and pliable and have high absorbency. They are used as wound dressing materials, controlled release delivery systems, cell culture, barrier media for preventing tissue adherence, and bioabsorbable implants. They also have various personal care applications, especially in oral hygiene, and can be used in food applications.

31 Claims, 2 Drawing Sheets

GELLED BIOPOLYMER BASED FOAM

CROSS-REFERENCE TO RELATED APPLICATIONS

This application is a divisional application of U.S. patent application Ser. No. 10/933,169, filed Sep. 2, 2004, incorporated herein by reference, which claims priority on U.S. Provisional Application 60/584,357, filed Jun. 30, 2004; U.S. Provisional Application 60/545,700, filed Feb. 18, 2004; U.S. Provisional Application 60/510,063, filed Oct. 9, 2003; and U.S. Provisional Application 60/501,500, filed Sep. 8, 2003, the disclosures of which are all incorporated herein by reference.

FIELD OF THE INVENTION

The invention relates to gelled biopolymer foams. In particular, this invention relates to a method for producing dried gelled biopolymer foams, to the resulting dried gelled foams, and to uses of the dried gelled foams in, for example, biomedical applications such as wound dressings, controlled release delivery systems, food applications, and personal care applications, such as cosmetic applications and oral hygiene.

BACKGROUND OF THE INVENTION

Biopolymer foams, especially gelled alginate containing foams, have been described for applications such as wound dressings, controlled release delivery systems, cell culture, barrier media for preventing tissue adherence, and bioabsorbable implants. However, these foams are either brittle, difficult to handle, and/or difficult to manufacture, requiring expensive equipment such as freeze dryers.

Two important functions of surgical or wound dressings are the ability to absorb and hold liquid and the ability to wick and transfer exudate of a wound away from the wound site. However, because wound healing is enhanced by keeping the wound bed moist, a wound dressing should absorb and transfer wound exudate away from the wound surface without desiccating the wound bed. Additionally, the wound dressing should release from the wound easily so that removal of the dressing does not damage the newly formed tissue.

Eagles, U.S. Pat. No. 5,80,777, and Bakis, U.S. Pat. No. 5,851,461, for example, each disclose methods of producing gelled polysaccharide foams that can be used as wound dressings. However, there is little or no control over the foam size and the resultant products are relatively difficult to handle. Polyurethane foams have also been used as wound dressings, but these foams do not contain biomaterials and are, consequently, not absorbable when used in implants. Eccard, U.S. Pat. Pub. No. 2003/0180242, discloses solid polymeric foams, but preparation of the foam requires heating and cooling of the reaction mixture to form the foam.

Thus, a need exists for a gelled foam that comprises biomaterials, has a high absorbency, is easy to manufacture and handle, and does not require expensive equipment, such as freeze dryers, for its manufacture.

SUMMARY OF THE INVENTION

In one aspect, the invention is a method for forming a dried gelled foam. The dried gelled foams are soft and pliable, yet have high absorbency and wet strength. The method can produce a foam with a physiological pH. The method allows control of the gelling rate and produces a mechanically homogeneous dried gelled foam. In addition, the method does not require expensive equipment, such as freeze dryers. The method comprises the steps of:

a) forming an aqueous dispersion comprising the following ingredients:
   i) a gel-forming polymer selected from the group consisting of alginate, pectic substances, carrageenans, glycol alginates, and mixtures thereof;
   ii) a gelling agent;
   iii) a water soluble plasticizer;
   iv) optionally, a foaming agent;
   v) a pH modifier; and
   vi) water;
in which the gel-forming polymer is dissolved in the water, and the gelling agent is dispersed in the water;

b) forming a foam from the dispersion, and forming a gelled foam; and c) drying the gelled foam to form the dried gelled foam; in which the dried gelled foam predominately comprises the plasticizer.

A preferred gel-forming polymer is alginate. A preferred gelling agent is calcium carbonate. Preferred water soluble plasticizers are glycerin, sorbitol, and mixtures thereof. When present, the preferred foaming agents are water soluble polymeric foaming agents, more preferably hydroxylpropyl methyl cellulose. A preferred pH modifier is glucono delta lactone. Drying the gelled foam may be carried out at ambient temperature or above and does not require freeze drying.

In another aspect, the invention is a dried gelled foam comprising a gel-forming polymer crosslinked with a polyvalent cation and a water soluble plasticizer. As described below, the dried gelled foams of the invention have numerous applications. They may be used as wound dressings. They may also be used in oral hygiene, in food and cosmetic applications, and as delivery systems for beneficial agents. Other applications are described herein.

DETAILED DESCRIPTION OF THE INVENTION

Figure 1:
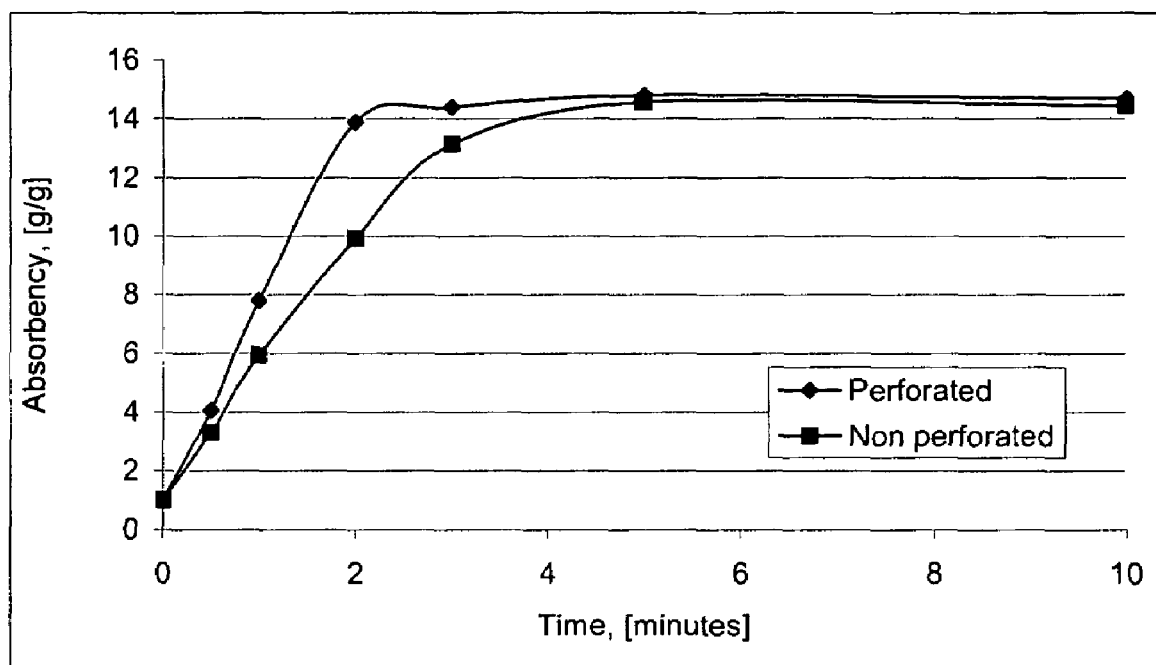
FIG. 1 shows the absorbance of model physiological fluid as a function of time for a perforated dried gelled foam and for a non-perforated dried gelled foam.

In the specification, examples, and claims, unless otherwise indicated, percents are percents by weight. Except where indicated by context, terms such as "gel-forming polymer," "gel-forming biopolymer," "gelling agent," "water soluble plasticizer," "foaming agent," "pH modifier," "divalent cation," "polyvalent cation," "co-binder," "additive," "beneficial agent," "cosmetic agent," "humectant," and similar terms also refer to mixtures of such materials. All temperatures are in ° C. (Celsius), unless otherwise indicated.

In one aspect, the invention is a method for forming a gelled dried foam using a gelling agent, a water soluble plasticizer; optionally, a foaming agent; a pH modifier; and a gel-forming biopolymer selected from the group consisting of alginates, pectin, carrageenan, glycol alginates, and mixtures thereof. The invention also includes applications of these dried gelled foams as disclosed herein.

INGREDIENTS

Gel-Forming Polymer

The gel-forming polymer is a water-soluble biopolymer selected from alginates, pectic substances, carrageenans, glycol alginates, and mixtures thereof.

Alginates are salts of alginic acid. Alginic acid, which is isolated from seaweed, is a polyuronic acid made up of two uronic acids: D-mannuronic acid and L-guluronic acid. The ratio of mannuronic acid and guluronic acid varies with factors such as seaweed species, plant age, and part of the seaweed (e.g., stem, leaf).

Alginic acid is substantially insoluble in water. It forms water-soluble salts with alkali metals, such as sodium, potassium, and, lithium; magnesium; ammonium; and the substituted ammonium cations derived from lower amines, such as methyl amine, ethanol amine, diethanol amine, and triethanol amine. The salts are soluble in aqueous media above pH 4, but are converted to alginic acid when the pH is lowered below about pH 4. A water-insoluble alginate is formed if certain polyvalent cations, especially calcium, barium, strontium, zinc, copper (+2), aluminum, and mixtures thereof are present in the medium at appropriate concentrations.

Water insoluble alginate salts, in which the principal cation is calcium, are found in the fronds and stems of seaweeds of the class Phaeophyceae, examples of which are *Fucus vesiculosus, Fucus spiralis, Ascophyllum nodosum, Macrocystis pyrifera, Alaria esculenta, Eclonia maxima, Lessonia nigrescens, Lessonia trabeculata, Laminaria japonica, Durvillea antarctica, Laminaria hyperborea, Laminaria longicruris, Laminaria digitata, Laminaria saccharina, Laminaria cloustoni,* and *Saragassum* sp. Methods for the recovery of alginic acid and its water-soluble salts, especially sodium alginate, from natural sources are well known, and are described, for example, in Green, U.S. Pat. No. 2,036,934, and Le Gloahec, U.S. Pat. No. 2,128,551.

Alginate may be reacted with an alkylene oxide, such as ethylene oxide or propylene oxide, to form a glycol alginate. The glycol is bonded to the alginate through the carboxyl groups. Typically, alginate is reacted with propylene oxide to form propylene glycol alginate (PGA). Preparation of propylene glycol alginate is disclosed in Strong, U.S. Pat. No. 3,948,881, Pettitt, U.S. Pat. No. 3,772,266, and Steiner, U.S. Pat. No. 2,426,125. Preferably, the propylene glycol alginate has a degree of esterification of about 40% to about 95%, more preferably about 70% to 95%. Mixtures of propylene glycol alginates of different molecular weights may also be used to effect a greater degree of stability to the wet foam.

Pectic substances include pectins and pectates. Pectin is a naturally occurring polysaccharide found in the roots, stems, leaves, and fruits of various plants, especially the peel of citrus fruits such as limes, lemons, grapefruits, and oranges. Pectins contain polymeric units derived from D-galacturonic acid. About 20-60% of the units derived from D-galacturonic acid, depending on the source of the pectin, are esterified with methyl groups. These are commercially known as high methoxy pectin and low methoxy pectin, the latter also including amidated pectins. Pectate (pectinate) is fully de-esterified pectin with up to 20% of the units derived from D-galacturonic acid.

Carrageenan refers to a group of sulfated galactans extracted from red seaweed. Carrageenans are linear chains of D-galactopyranosyl units joined with alternating (1→3) α-D and (1→4) β-D-glycosidic linkages. Carrageenans may, in part, be distinguished by the degree and position of sulfation. Most sugar units have one or two sulfate groups esterified to a hydroxyl group at carbons C-2 or C-6. There are three main types of carrageenan, kappa carrageenan, iota carrageenan, and lambda carrageenan. Kappa carrageenans produce strong rigid gels while those made with iota products are flaccid and compliant. Lambda carrageenans do not gel in water. A preferred carrageenan is iota carrageenan. Iota carrageenan has a repeating unit of D-galactose-4-sulfate-3,6-anhydro-D-galactose-2-sulfate providing a sulfate ester content of about 25 to 34%.

A preferred gel-forming polymer is alginate. When alginate is used as the gel-forming polymer, the aqueous dispersion typically comprises about 0.5 wt % to about 10 wt %, preferably about 1 wt % to about 6 wt %, more preferably about 2 wt % to about 4 wt % of the alginate. This produces a dried gelled foam that comprises about 3 wt % to about 45 wt %, preferably about 6 wt % to about 37 wt %, more preferably about 12 wt % to about 25 wt % of alginate, exclusive of water and additives. Suitable alginates have a weight-average molecular weight of about 20,000 Daltons to about 500,000 Daltons. Weight-average molecular weight is calculated by first determining the intrinsic viscosity, then using the Mark-Houwink Sakurada Equation, as in Martinsen, et al; "Comparison of Different Methods for Determination of Molecular Weights and Molecular Weight Distribution of Alginates" (*Carbohydr. Polym.*, 15, 171-193, 1991).

The preferred molecular weight range may depend on the application of dried gelled foam. When a higher molecular weight alginate is used, such as a molecular weight of 300,000 Daltons, the resulting foam is readily rewettable or rehydrateable after drying. For applications in which it is desired for the dried gelled foam to disintegrate and/or dissolve in water or aqueous media, such as in certain food and pharmaceutical applications, lower molecular weights, such as about 20,000 Daltons to about 150,000 Daltons, may be desirable. For applications in which it desirable for the dried gelled foam not to disintegrate in water or other aqueous media, such as in wound dressing applications, higher molecular weights, such as about 150,000 Daltons to 500,000 Daltons, may be desirable.

Alginate forms viscous solutions in water. However, when higher concentrations of alginate are used to prepare the aqueous dispersions, it may be necessary to use a lower molecular weight alginate, for example an alginate with a molecular weight of 150,000 instead of an alginate with a molecular weight of 300,000, to produce a processable dispersion. The highest molecular weight alginate that produces a processable dispersion should be used to produce dried gelled foams with the highest mechanical strength. However, as noted above, for certain applications, in may be desirable to use an alginate with a lower molecular weight to produce a dried gelled foam that, for example, readily disintegrates and/or dissolves in water.

Gelling Agent

The gelling agent comprises a polyvalent cation, typically a divalent and/or a trivalent cation, or a mixture of polyvalent cations capable of gelling the gel-forming polymer. Suitable polyvalent cations include, for example, calcium (2+), barium (2+), strontium (2+), iron (2+), zinc (2+), copper (2+), and aluminum (3+). Preferred cations are divalent metal cations, more preferably the calcium (2+) cation.

A salt or combination of salts that provides the desired gelling polyvalent cation or mixture of polyvalent cations can be used as the gelling agent, so long as the resulting composition is not capable of forming a gel until addition of the pH modifier. The gelling agent may insoluble in water, but releases an ion capable of forming a gel in acidic solution, typically at a pH of 3 or higher. Alternatively, the gelling agent may be soluble in water but the ion capable of forming a gel is complexed and becomes available only under acidic conditions. Useful gelling agents include salts, such as the following, their hydrates, and mixtures thereof: calcium carbonate, calcium disodium edetate, calcium oxalate, dicalcium phosphate, tricalcium phosphate, tricalcium citrate, strontium carbonate, barium carbonate, cupric carbonate, zinc carbonate, zinc oxalate, and zinc phosphate. Zinc may be beneficial for wound healing and, for example, could be used in combination with another polyvalent cation such as calcium. WO 00/19979 discloses that gelled foams that comprise copper and zinc are more resistant to the deleterious effects of sterilization. Barium may cause the dried gelled foam to be substantially opaque to X-rays so that it can be used as a medical implant in radiography.

Preferred gelling agents are those that also provide a buffering effect and/or consume acid when the polyvalent cation is released. These include for example, bicarbonates, carbonates, and phosphates, preferably carbonates. A preferred gelling agent, especially for alginate, pectic substances and iota carrageenan, is calcium carbonate. Calcium carbonate not only provides the cation necessary for gel formation, it also can provide a gelled foam which has a pH in range of about 4 to 8, which is desirable for certain applications, such as wound healing and cell growth. Aluminum ion is useful for gelling glycol alginates, which typically do not gel with calcium-ion.

The concentration of gelling agent may be controlled so that the resulting gelled foam contains gelling sites that are not reacted with divalent cations; i.e., the polyvalent cation or mixture of polyvalent cations is present in a molar amount less than that required to saturate 100% of the gelling sites of the gel-forming polymer. For example, when sufficient polyvalent cations are present to react with all available gelling sites (L-guluronic acid units in the case of alginate, D-galacturonic acid units in the case of pectin substances) the gel-forming polymer is saturated.

The amount of cation required to completely saturate the gelling sites of alginate, for example, is considered to be 1 mole of divalent cation per 2 moles of L-guluronic acid in the gel-forming polymer or 1 mole of trivalent cation per 3 moles of L-guluronic acid in the alginate when only a divalent cation or only a trivalent cation is used in the gelling. When a mixture of a divalent cation or cations and a trivalent cation or cations is used, the amounts required to saturate the alginate can be determined because a divalent cation occupies two gelling sites and a trivalent cation occupies three gelling sites. Thus, any amount less than this is considered to be an amount less than that required to completely saturate the gelling sites of the alginate. Typically, the cation or cations added are sufficient to saturate about 10% to 200%.

The saturation may depend on the application of dried gelled foam. For applications in which it is desired for the dried gelled foam to disintegrate and/or dissolve in water or aqueous media, such as in certain food and pharmaceutical applications, lower saturation, such as about 10% to 60%, or 20% to 55%, may be desirable. For applications in which it desirable for the dried gelled foam not to disintegrate in water or other aqueous media, such as in wound dressing applications, higher saturation, such as about 60% to 200%, or 65% to 200%, may be desirable.

In alginate, the strength of gels formed by reaction of alginate with polyvalent cations is related to the guluronic acid content ("G content") of the alginate as well as the arrangement of guluronic and mannuronic acids on the polymer chain. The G content of the alginate is at least about 30%, preferably about 40% to about 90%, and more preferably about 50% to about 80%. Alginate derived from, for example, *Lessonia trabeculata* and from the stems of *Laminaria hyperborea* have the necessary G content and can be used to form the gelled foams of the invention. Fully saturated alginates with a high G content give dried gelled foams with the highest mechanical strength.

The amount of divalent cation, such as calcium, required to react stoichiometrically with these G-blocks can be calculated for each alginate type by considering that two guluronic acid units plus one divalent cation are required to create one ionic crosslink. The amount of calcium required for stoichiometric saturation of a 1% sodium alginate solution are given in the following table:

| Seaweed Source | % G | mM Ca |
|---|---|---|
| *Laminaria hyperborea* (stem) | 70 | 14-16 |
| *Laminaria hyperborea* (leaf) | 54% | 11-13 |
| *Lessonia trabeculata* | 68% | 13-15 |
| *Macrocystis pyrifera* | 39% | 8-9 |

A list of various commercially available alginates, their properties, and their sources is found in Shapiro, U.S. Pat. No. 6,334,968, Table 1, column 16, line 49, to column 17, line 18, incorporated herein by reference. Mixtures or blends of alginates, for example alginates of different molecular weights and/or G content, may be used as the gel-forming polymer.

Complete saturation (100% saturation) of the gelling sites occurs when the composition contains 1 mole of divalent cation per 2 moles of L-guluronic acid units. For example, an about 15 mM solution of calcium ion is required to 100% saturate a 1% solution of sodium alginate extracted from the stems of *Laminaria hyperborea*, an about 12 mM calcium solution is required to 100% saturate a 1% solution of sodium alginate extracted from the leaves (fronds) of *Laminaria hyperborea*, and an about 14 mM solution of calcium ions is required to 100% saturate a 1% solution of sodium alginate extracted from *Lessonia trabeculata*. Thus, when alginate is used as the gel-forming polymer, the gel-forming composition preferably comprises 0.2 to 0.9 mM of divalent cation, preferably calcium (2+) ion, per 2 mM of L-guluronic acid units present in the alginate. The extent of crosslinking can be controlled by controlling either the amount of gelling agent, for example, calcium carbonate, and/or the amount of pH modifier, for example, glucono delta-lactone, present during gel formation. The extent of crosslinking can also be controlled by timing of the drying. By initiating and completing the drying before the all the calcium is released and reacted with the alginate, the cross-linking will be done to a lesser extent compared to a longer gelling time before the drying process As will be apparent to those skilled in the art, mechanical strength is a function of alginate molecular weight and G content as well as the degree of saturation, drying time, and other process variables described herein. Thus, the properties of the dried gelled foam may be varied and optimized for a particular application by variation of these variables. Further, it may be that several different combinations of these variables may produce dried gelled foams with the desired properties.

When all the sites on the gel-forming polymer are not saturated with crosslinking polyvalent cations, the remaining sites are occupied by non-crosslinking cations, typically monovalent cations. Active cations, such as the Ag (1+) cation, may be used to occupy some or all of the remaining sites. Scherr, U.S. 2003/0021832 A1, discloses that silver alginate may be used for the treatment of burns, wounds, ulcerated lesions, and related pathological states.

Complementary binders ("co-binders"), such as chitosan and its derivatives, high M-content alginates, hyaluronate, carboxymethyl cellulose, starch, modified starch, modified alginates, such as crosslinked alginates and glycol alginates, such as propylene glycol alginate, may also be added. These water soluble co-binders do not themselves form gels in water under the conditions at which gel formation takes place. Glycol alginates and lambda carrageenan, for example, may used as co-binders when calcium ion is used to form the gel in water because these materials do not form gels in water with calcium ions. "Modified starch" refers to starch that has undergone some chemical modification, such as reaction with a cyclic anhydride, especially a cyclic anhydride that contains a substituent group comprising 5 to 18 carbon atoms, preferably 1-octenylsuccinic anhydride ("OSAN-starch," sometimes called "lipophilic starch"). The approximate amount of substitution is reported to be about 2% to 3%. Modified starch and processes for its preparation are disclosed in Caldwell, U.S. Pat. No. 2,661,349. Hyaluronan is unsulphated glycosaminoglycan, whose molecular weight ranges from 300 kDa to 2000 kDa depending on the source from which it is isolated.

Although these water soluble co-binders do not themselves form gels in water under the conditions at which gel formation takes place, they may be added to impart some beneficial property to the dried gelled foam, such as strength, adhesion, bioactivity, etc. Hyaluronan, for example, also provides a cosmetic effect. An gel-forming alginate with a high G-content may be used as the gelling agent in combination with an alginate with a high content of mannuronic acid (high M-content), about 70 to 100% M, as an added co-binder. Although high M-content alginates do not gel, they have beneficial bioactive properties and would impart these beneficial properties to the resulting dried gelled foam.

Water Soluble Plasticizers

The aqueous dispersion comprises a water soluble plasticizer. A plasticizer provides flexibility and softness to the gelled foam so that the resulting dried gelled foam is soft and pliable. The plasticizer also enhances the reabsorption of water by the dried gelled foam.

Typical plasticizers are polyhydric alcohols such as glycerin, sorbitol, ethylene glycol, propylene glycol, and polyethylene glycol. Preferably, the plasticizer is non-toxic and does not affect the solubility of the gel-forming polymer. Plasticizers such as ethylene glycol and polyethylene glycol affect the solubility of alginate. This adversely affects the drying of the foam, producing a brittle foam. Preferred plasticizers include sorbitol and glycerin. Glycerin and sorbitol are biocompatible and do not affect the solubility of alginate.

The ratio of plasticizer to gel-forming polymer is such that the resulting gelled foam, exclusive of water and additives, is predominately plasticizer. The ratio of plasticizer to alginate in the aqueous dispersion is suitably about 10:1 to about 2:1, typically about 9:1 to about 2.5:1, more typically about 8:1 to about 3:1, and even more typically about 6:1 to about 4:1. Dried gelled foams with a high concentration of plasticizer are soft and pliable, as required for, for example, wound dressing applications. A high concentration of plasticizer may also cause the dried gelled foam to have a sticky surface, but decreasing the plasticizer concentration will make the dried gelled foam harder. Preferably the dried gelled foam, exclusive of water and additives, is predominantly comprised of the plasticizer. Typically, the plasticizer comprises more that 50 wt %, more typically more than 55 wt %, of the dry gelled foam, exclusive of water and additives such as silica.

Because of the plasticizer is the predominant ingredient in the dried gelled foam (exclusive of water and additives), the calculated absorbency (foam weight after absorption/dry weight of the dried gelled foam) of the dried gelled foam increases as the plasticizer concentration decreases. An absorbency of about 10 to about 17 grams of liquid, typically an aqueous liquid, per gram of dried gelled foam is observed. Typically, the dried gelled foams absorb between about 50 to 60 g of liquid per 100 $cm^2$ of 5 mm thick dried gelled foam. However, foams that can absorb up to about 65 g of liquid per 100 $cm^2$ of 5 mm thick foam have been prepared.

Foaming Agent

A foaming agent may be included in the aqueous dispersion to aid in foaming. When present, the foaming agent must produce a foam that lasts until gelation occurs. This time period will depend on the conditions chosen for foam formation, but will typically be about half an hour or less at room temperature. The foaming agent may be a single material or a mixture of materials that aid in foaming. Depending on the application for the dried gelled foam, the foaming agent may be a polymeric foaming agent, a surfactant, or a mixture thereof.

Polymeric foaming agents, such as surface active hydrocolloids, are generally preferred for most applications because they are harder to leach from the resulting gelled foam than surfactants. Examples of surface active hydrocolloids include methyl cellulose, hydroxy propyl methyl cellulose (HPMC), hydroxy propyl cellulose (HPC), hydroxy ethyl cellulose (HEC), and glycol alginates, such as propylene glycol alginate. For some applications, it may be advantageous to add an additional polysaccharide, for example a cellulose derivative such as carboxymethyl cellulose, in addition to the foaming agent.

The polymeric foaming agent is preferably soluble in water so that a homogeneous gelled foam is produced. A preferred water soluble foaming agent is hydroxy propyl methyl cellulose. Hydroxy propyl methyl cellulose produces small bubbles that last until gelation occurs.

When dried gelled foams containing high levels of calcium are soaked in water, the foam structure does not break down due to the high level of crosslinking of the foam. However, the soluble components in the foam, including water soluble foaming agents such as hydroxy propyl methyl cellulose, will diffuse out of the foam. This loss of foaming agent may be prevented in, for example a wound healing application, by use a foaming agent that is not soluble under conditions of use. Some foaming agents form gels at body temperature, for example methyl cellulose forms gels above 35° C. When using a foam that comprises methyl cellulose as the foaming agent in an application in which the foam is at body temperature, the methyl cellulose will stay in the gelled state and remain in the foam and contribute to the wet strength of the foam.

When a polymeric foaming agent such as hydroxy propyl methyl cellulose is used, the concentration of the polymeric foaming agent in the aqueous dispersion is typically about 0.5 wt % to about 6 wt %, preferably about 1 wt % to about 4 wt %, more preferably about 1.5% to about 2 wt %. This produces a dried gelled foam that comprises about 3 wt % to about 37 wt %, preferably about 6 wt % to about 25 wt %, more preferably about 6% to about 12.5 wt %, of the polymeric foaming agent, excusive of water and any additive or additives that may be present in the foam.

For certain applications, a surfactant, with or without an added polymeric foaming agent, may be used as the foaming agent. Surfactants are well known to those skilled in the art and are described, for example, in *McCutcheon's Detergents and Emulsifiers*, and Laughlin, U.S. Pat. No. 3,929,678, incorporated herein by reference. Nonionic surfactants are typically condensation products of a hydrophobic organic aliphatic or alkyl aromatic compound and hydrophilic ethylene oxide and/or propylene oxide. The length of the resulting polyether chain can be adjusted to achieve the desired balance between the hydrophobic and hydrophilic properties. Nonionic surfactants include, for example, ethoxylates of alkyl phenols containing from about 8 to 18 carbon atoms in a straight- or branched-chain alkyl group, such as t-octyl phenol and t-nonyl phenol with about 5 to 30 moles of ethylene oxide, for example nonyl phenol condensed with about 9.5 moles of ethylene oxide, dinonyl phenol condensed with about 12 moles of ethylene oxide; ethoxylated and propoxylated alcohols, especially $C_{10-20}$ alcohols, with 2 to 100 moles of ethylene oxide and/or propylene oxide per mole of alcohol, especially ethoxylates of primary alcohols containing about 8 to 18 carbon atoms in a straight or branched chain configuration with about 5 to 30 moles of ethylene oxide, for example, the ethoxylates of decyl alcohol, cetyl alcohol, lauryl alcohol, or myristyl alcohol; ethoxylates of secondary aliphatic alcohols containing 8 to 18 carbon atoms in a straight or branched chain configuration with 5 to 30 moles of ethylene oxide; condensation of aliphatic alcohols containing about 8 to abut 20 carbon atoms with ethylene oxide and propylene oxide; polyethylene glycol and polyethylene oxide; ethoxylated castor oil (CREMOPHOR® CO 40); ethoxylated hydrogenated castor oil; ethoxylated coconut oil; ethoxylated lanolin; ethoxylated tall oil; ethoxylated tallow alcohol; and ethoxylates of sorbitan esters such as polyoxyethylene sorbitan monolaurate (TWEEN® 20), polyoxyethylene sorbitan monopalmitate (TWEEN® 40), polyoxyethylene sorbitan monostearate (TWEEN® 60) polyoxyethylene sorbitan monooleate (TWEEN® 80), and polyoxyethylene sorbitan trioleate (TWEEN® 85). For physical applications such as wound dressings, when a surfactant is included in the dried gelled foam, non-ionic surfactants, such as the ethoxylates of sorbitan esters, are preferred. Examples of anionic surfactants are sodium stearate, sodium cetyl sulfate, sodium lauryl sulfate, ammonium lauryl sulfate, triethanolamine lauryl sulfate, sodium myristyl sulfate, and sodium stearyl sulfate, triethanol amine dodecylbenzenesulfonate, sodium dodecylbenzene sulfonate, sodium polyoxyethylene lauryl ether sulfate, and ammonium polyoxyethylene lauryl ether sulfate. A preferred anionic surfactant is sodium lauryl sulfate (sodium dodecyl sulfate). Cationic surfactants include, for example, quaternary ammonium salts, such as cetyl trimethylammonium bromide, lauryl trimethyl ammonium chloride, alkyl benzyl methyl ammonium chlorides, alkyl benzyl dimethyl ammonium bromides, cetyl pyridinium bromide, and halide salts of quaternized polyoxyethylalkylamines. Zwitterionic surfactants can also be used.

When the surfactant is used with a polymeric foaming agent, a useful surfactant is a sorbitan ester, such as TWEEN® 20 surfactant. When a surfactant, such as TWEEN® 20 surfactant, is used with a polymeric foaming agent, the dried gelled foam may comprise about 0.05 wt % to 1.0 wt %, typically 0.1 wt % to 0.5 wt %, of the surfactant. However, for certain applications, such as oral care applications in which a surfactant, such as, for example, sodium lauryl sulfate, is used without a polymeric foaming agent, the dried gelled foam may comprise about 0.5 wt % to 5.0 wt %, typically 1.5 wt % to 3.0 wt %, of the surfactant, excusive of water and any additive or additives, such as silica or other abrasives or polishing agents, that may be present in the foam.

pH Modifier

The pH modifier is added during preparation of the foam to release the polyvalent cation from the gelling agent. Typically, the pH modifier lowers the pH of the aqueous dispersion. As the pH of the composition is lowered, the polyvalent cation becomes available. The polyvalent cation reacts with the gelling sites of the gel-forming polymer, and gelation takes place.

Various materials, especially those that slowly generate an organic acid that buffers the gel-forming composition, may be used as the pH modifier. Preferably, the pH is slowly lowered during gel formation. Thus, a pH modifier that slowly lowers the pH is preferred. Acids that provide a buffering action and/or materials that slowly generate acid, such as anhydrides, esters, amides, lactones, and lactams, which slowly generate acids by chemical reaction, can be used as the pH modifier. These include, for example, lactic acid lactone, glycolic acid lactone, and glucono delta lactone. Combinations of materials, in which one slowly generates acid and the other provides a buffering effect, may be used.

A preferred pH modifier is glucono delta-lactone (gluconic acid δ-lactone), but other pH modifiers that slowly lower the pH may also be used in addition to or in place of glucono delta lactone. Glucono delta-lactone (GDL) slowly reduces the pH; allowing gelation to occur in a very controlled manner, which aids formation of a mechanically homogeneous foam with optimum strength. If gel formation takes place before agitation and foaming is complete, the gel formed during this period will be destroyed, so that the resulting foam will have less than optimum strength.

A ratio of pH modifier to gelling agent that will produce a dried gelled foam with a pH in the rage of 4 to 8 is preferably used. This ratio is typically about 1 equivalent of pH modifier to 1 equivalent of gelling agent, or higher.

Other Ingredients or Additives

As described below, other ingredients, known as additives, such as abrasives, food, and/or beneficial agents such as pharmaceutical active ingredients ("actives") and/or cosmetic agents, may be included in the dried gelled foam for specific applications. "Additives" thus include ingredients other than the gel-forming polymer, gelling agent, plasticizer, foaming agent, co-binder, pH modifier, and components derived there from, such as calcium ions derived from the gelling agent. Many of these additives may be added to the aqueous dispersion during formation of the foam so that a dried gelled foam containing the desired additive or additives is formed. Solid additives, such as silica, may be added in this manner.

In addition, the dried gelled foam can absorb both hydrophilic and lipophilic liquids, so many additives may be added after the foam is formed. Liquids that do not hydrate the dried gelled foam are absorbed into the foam by capillary action so that additional additives may be added to the foam after it has been dried. Thus, degradation and loss of volatile materials during foam formation and drying is avoided, and materials that might adversely affect foam formation may be added after the foam has been dried. Examples of such materials include flavors and fragrances, and solutions or suspensions of active materials, such as those described below, in lipophilic liquids such as an alcohols, oils, polyethylene glycol or other solvents that does not hydrate the dried gelled foam. Additional polymers, such as chitosan, iota-carrageenan, kappa-carrageenan, lambda-carrageenan, and mixtures thereof, may be added to the surface of the dried gelled foam by this technique. Although carrageenan can be used as the gel-forming polymer, it can also be used as additive, when added to the dried gelled foam after gel formation. Chitosan, which is sometimes regarded as a cellulose derivative in which the C-2 hydroxyl groups have been replaced by amino groups, binds strongly to alginate due to electrostatic interactions.

Water containing water-soluble components, such as water soluble dyes or water soluble silver salts, may also be added to the dried gelled foam in small amounts, but the hydration of the dried gelled foam may alter its appearance and performance after the water has evaporated.

Gelled Foam Preparation

The structure of a gelled foam is set by ionic crosslinking of the gelling sites of the polymer chains of the gel-forming polymer. Each ionic crosslink is formed by an ionic reaction between a polyvalent cation and gelling sites that are located on different polymer chains. Ionic reaction to link polymer chains is not the same as, and should not be confused with, crosslinking in which a chemical bond, for example, a carbon-carbon bond or a carbon sulfur bond, is formed between two polymer chains.

In preparing the gelled foam, the ingredients that form the gelled foam are first dissolved or dispersed in water. The water used to form the aqueous dispersion should not contain ions, such as calcium, that can crosslink the gel-forming polymer. Because crosslinking polyvalent cations, such as calcium, from any source, including the water used to form the dispersion, can crosslink the gel-forming polymer, deionized or distilled water is preferred for formation of the aqueous dispersion.

Although these ingredients may be added in any order, one method is to first form an aqueous dispersion containing the gel-forming polymer, the plasticizer, and the gelling agent. The dispersion is stirred to dissolve the gel-forming polymer and the plasticizer and to disperse the gelling agent. After the gel-forming polymer has dissolved and the gelling agent has been dispersed, the foaming agent and the pH modifier are added. If foaming agent is used, it is may be added after the gel-forming polymer and the plasticizer have dissolved and the gelling agent has been dispersed so that foam will not be formed until these materials have been uniformly distributed in the aqueous dispersion.

Alternatively, the foaming agent may be added to the aqueous dispersion containing the gel-forming polymer, the plasticizer, and the gelling agent. The gel-forming polymer, the plasticizer, and the gelling agent are then dispersed or dissolved at low shear so a foam is not formed. After the gel-forming polymer, the plasticizer, and the gelling agent are dissolved or dispersed, the shear is increased to form the foam.

If the pH modifier is added before the alginate has completely dissolved, it may be difficult to form a homogeneous foam. Before the pH modifier is added to an aqueous dispersion that contains a gelling agent, the polyvalent cation of the gelling agent is not available to crosslink the gel-forming polymer. Consequently, the aqueous dispersion will not gel in the absence of a pH modifier. Thus, to prevent premature gel formation or pregelation, it is advantageous to add the pH modifier after the gel-forming polymer and the plasticizer have dissolved and the gelling agent has been dispersed in the aqueous dispersion.

The pH modifier may be added before or after formation of the foam. In one method, a foam is formed from an aqueous dispersion that comprises all the ingredients but the pH modifier by agitating the aqueous dispersion for several minutes. The pH modifier is added, and agitation continued for several additional minutes. The pH modifier can be added as a powder or in solution. A preferred solution is between 5 and 25% glucono delta-lactone (GDL) in water. Because water slowly converts glucono delta-lactone to gluconic acid, the glucono delta-lactone solution is preferably used within 15 min of preparation, more preferably within 5 min. When the pH modifier is added to an aqueous dispersion that contains a gelling agent, the polyvalent cation is solubilized or otherwise becomes available to react with the gelling sites due to the decrease in pH brought about by the pH modifier. Preferably the pH modifier slowly lowers the pH of the gel-forming composition. This slow release of polyvalent cations provides a gelled foam that is mechanically homogeneous.

The time for the foam to gel may be controlled by varying the size of the particles of the gelling agent. If the particles are too large, the gel time may be unacceptably long for most applications. When small particles of gelling agent are used, the smaller particles have a greater surface area for reaction, and, consequently, the polyvalent cation is released more quickly. Thus, gel formation occurs relatively more quickly than when large particles of gelling agent are used. When the particles are, on average, about 0.28 µm or less, the initial gel time is less than 3 min. Therefore, when small particles, the pH modifier should be added immediately before the foam is shaped to form a final product, such as by being poured into a mold. When the particles are, on average, about 3.3 µm the initial gel time is about 20 min at room temperature. When the particles are, on average, about 21 µm the initial gel time is about 30 min at room temperature. The time for maximum gelling can be varied from about 2.5 hours to over 16 hours by controlling the particle size of the gelling agent. As will be apparent to those skilled in the art, a high initial rate of crosslinking, followed by a slower rate of cross-linking, can be attained by the use of a mixture of large and small particles.

A foam is formed from the aqueous dispersion. Foaming may be carried out by well known methods. The foam may be produced by beating, stirring, or otherwise mechanically agitating the aqueous dispersion. Both batch and continuous mixing and foaming may be carried out. Foaming may involve the introduction of a gas, such as air, into the aqueous dispersion, and shearing of the aqueous dispersion to create a mixing effect, which may produce a very fine dispersion of gas bubbles in the dispersion. In the early stages of foaming, when the total amount of gas entrained in the dispersion is small, the gas bubbles may be substantially spherical in shape. As the total volume of gas entrained in the dispersion increases, the gas bubbles may change to a substantially polyhedral shape, with the dispersion distributed in thin membranes between adjacent gas bubbles and in ribs or spokes where several gas bubbles come into very close proximity to each other. The result is a foam having gas dispersed in a cellular structure.

The density, absorbency, and softness of the dried gelled foam can be varied by varying the blending time. Short blending times provide more compact foams with higher wet densities than the softer and fluffier foams obtained after longer periods of aeration. Foams produced at lower aeration times have better flow properties, which are useful when the gelled foam is to be poured into a mold. However, gelled foams with lower densities, produced at longer aeration times, absorb liquid faster. Depending on the amount of agitation, wet foams with a wt density of about 0.1 g/ml to about 0.4 g/ml, which after drying produce dry gelled foams with densities of about 0.04 g/ml to about 0.09 g/ml, may be produced. Alternatively, the foam may be produced other methods known in the art. The foam may be produced, for example by blowing a gas into the solution, by applying a vacuum to the solution, or by extruding the aqueous dispersion through a die under pressure.

The wet gelled foam may be cast as a layer or as a shaped article. For example, the foam may be cast as a layer on a substrate, which may be a woven or non-woven fibrous article, a film, or another dried gelled foam. The substrate may comprise, for example, an assemblage of fibers or yarns, such as cotton, linen, silk, nylon, polyester, rayon, polysaccharide such as alginate, polylactide, and blends thereof, a non-woven material, such as TYVEK® spunbonded polyethylene, or a material such as paper or a polymer film. The gelled foam may be cast as a thin foam layer having a thickness up to about 1 mm. Alternatively, the gelled foam may be cast as a thick foam layer having a thickness of up to about 30 mm. A convenient dry thickness for a wound dressing is about 2 mm to about 10 mm, typically about 5 mm. Alternatively, the wet gelled foam can be applied to, for example, the skin, formed, and allowed to dry in place.

The gelled foam is dried after its formation. The gelled foam may be dried at ambient temperature, or with slight heating to, for example, about 40° C. to 100° C., by placing the gelled foam in an oven or by blowing warm air over the foam. Alternatively, the dried foam may be dried with infrared heating. Drying can be carried out in a batch or continuous process. It is unnecessary to freeze dry the gelled foam. An advantage of this invention is that freeze drying of the gelled foam is unnecessary and not preferred. To increase the wet tensile strength of the dried gelled foam after rehydration and yet minimize drying time, it is advantageous to initially dry the foam at or only slightly above room temperature and then to increase the drying temperature. For example, the foam may be dried at 40° C. for about 1 hr, then at about 60° C. for about 2 hr, and then at about 80° C. for about 1 hr.

When a gelled foam is formed by treating a preformed foam with acid, the resulting gelled foam is not mechanically homogeneous because of the diffusion of the acid necessary release the polyvalent cations from the gelling agent and gel the foam. However, the method of the invention produces gelled foams that are mechanically homogeneous. Mechanically homogenous means that the reacted gelling sites of the gel-forming polymer are evenly distributed throughout the solid phase of the gelled foam.

Beads of gelled foam may be formed by adding pieces of the wet foam to an organic liquid, typically an organic liquid which is miscible with water or in which water is partly soluble, for example, a lower alcohol, such as methanol or ethanol, or a ketone such as acetone. Typically, the bath will also contain some of the plasticizer to prevent the organic liquid from leaching the plasticizer out of the foam. Because the organic solvent precipitates the alginate and prevents it from being crosslinked by the calcium ion, the amount of crosslinking by the calcium ion can be controlled by the length of time between foaming and addition of the foam to the organic liquid and by the length of time the foam is allowed to remain in the organic liquid.

For biomedical applications, the dried gelled foam will typically be sterile and enclosed in a sterile packaging. The dried gelled foam may be sterilized using sterilization techniques known in the art such as gamma radiation, steam and heat sterilization, electron beams, or chemical sterilization, such as with ethylene oxide.

The dried gelled foam may be compressed for ease of packaging, transportation, and storage. The dried gelled foams may be readily compressed to up to about one sixth their volume by pressing on them with a weight. Compressed dried gelled foams have the same absorbency as uncompressed dried gelled foams, indicating that compressing the dried gelled foams not change their absorbency.

The dried gelled foams may be perforated to increase the rate at which liquid is taken up. The perforated dried gelled foams take up liquid more rapidly than non-perforated foams, but the amount of liquid taken up by the foams is the same.

Two or more layers of foam with same and/or different physical properties and/or chemical ingredients (such as different active ingredients, colors, etc.) can be laminated together to create multiple layered foams with various benefits, such as the delivery of otherwise non-compatible beneficial agents at the same time. This technique can be used to build in desired release characteristics of beneficial agents, desired texture, absorbency profiles and desired appearance. This can be performed by attaching two or more layers of dry sheets of foam. Alternatively, a second layer of wet foam can be cast onto a first layer of wet or dried foam. When making foams with multiple layers is possible to add colored article, figures, films or shapes that can be entrapped in-between the layers. These figures will not be visible in a dry foam, but appear when the foam is absorbing liquid and becomes transparent.

Foam mass at certain stage of gelation and drying can be extruded in different shapes that on further drying could produce various shaped 'foam' bodies. This process could be especially useful to create spherical shaped objects for personal and oral care applications.

INDUSTRIAL APPLICABILITY

The high absorbency properties of the dried gelled foam make it useful in numerous applications, such as in diapers and sanitary products and in products for absorbing spillage and liquid waste including hazardous waste. In some of these applications it is a benefit that the materials are non-toxic, well-tolerated and biodegradable, meaning that the absorbing material will not harm wastewater treatment processes and so may be readily disposed of using the normal processes of sewage disposal. Various ingredients may be added to the dried gelled foam for specific applications. For, example activated charcoal in powdered or granular form may be added to absorb undesirable compounds from the air, such as odors.

The dried gelled foam is useful as a wound dressing. The wound dressing combines many of the desirable wound dressing properties, including, for example: high absorbency; high flexibility; vertical wicking; non-adherence to the wound; high dry strength; high wet strength; calcium donation; and a non-shedding matrix. Further, antimicrobial agents, such as silver, silver salts, and/or chitosan may be incorporated into the dressing.

Wound dressings are the primary dressing placed in direct contact with the wound, or as near as practical against the wound. Wound dressings may be used on injured tissue and for bodily fluid drainages where control and management of fluid and secretions is desired. The dressings may, if required, be secured into position with any suitable secondary wound dressing such as a wrap, tape, gauze, or pad. The dressings are temporary, however, and are not incorporated into the healed tissues. For wound dressing applications the foam typically will have a pH from about 6.0 to about 8.0, more typically about 6.0 to about 7.0.

The wound dressing may comprise a layer of the foam on a substrate, which, as described above, may be a woven or non-woven fibrous article, a film or another dried gelled foam. Alternatively, the dried gelled foam may be used as a would dressing without a support. Alternatively, the foam may be shaped around a wound in the ungelled state and allowed to gel in place.

The dressing may also contain a wicking layer between the gelled foam and the substrate. The wicking layer provides absorbency, but more importantly it encourages moisture to move from the wound facing side of the dressing to the back of the dressing where it escapes out of the dressing through a breathable backing. It should have good wicking properties so that moisture can be spread over as large a surface area as possible, thus increasing evaporation. The overall effect of this layer is to draw moisture from the gelled foam, thus decreasing the chances of wound maceration, and to increase evaporation through the backing of the dressing. The wicking layer may be formed of several plies (which may or may not be the same) if desired, but it is preferred that the total thickness of the wicking layer does not exceed 1 mm. Suitable materials for the wicking layer include nonwoven, woven and knitted fabrics. Nonwoven viscose fabrics such as those conventionally used for making nonwoven surgical swabs are preferred, but many alternative fabrics, particularly other cellulosic fabrics, could be used in their place.

A growth hormone or a polypeptide growth factor may be incorporated into the dried gelled foam before, during, or after foam formation to aid in wound healing. Bacteriostatic and bactericidal materials, such as silver, silver salts, and chlorohexidine; antibiotics such as penicillin; vitamins such as ascorbic acid; enzymes such as pepsin and trypsin; pain relieving agents; and materials such as thombin and fibrinogen may also be incorporated into the dried gelled foam before, during, or after foam formation.

The dried gelled foam is useful as a cell culture replicating medium. The cells to be replicated can be disposed in the pores in the foam. The cell culture replicating medium may constitute an implant, typically a bioabsorbable implant. Cultured cells, such as mammalian cells, may be disposed in the pores of the implant, which may then be implanted surgically in a human or animal body. The implant may encourage tissue growth in and around the implant in vivo.

The dried gelled foam may serve as a bioabsorbable barrier medium that can be implanted to prevent post surgical tissue adherence.

The dried gelled foam may be used as a controlled release delivery system, or as a delivery system, for beneficial agents, such as, for example: antibiotics, antibacterial agents, antifungal agents, antiseptics, anti-inflammatories, agents for the treatment of cancer, nutritional agents, living cells, etc. The hydrated gelled foams present a low diffusion barrier to water soluble molecules so that water soluble beneficial agents will rapidly diffuse out of the hydrated foam. The delivery system may be taken directly. Or the delivery system may be prehydrated in water or an aqueous liquid, such as milk or a beverage, or partially or completely dissolved in water or an aqueous liquid being placed in the oral cavity.

The beneficial agent may be a drug or pharmaceutical active, which can be administered to a patient transdermally. The beneficial agent may be included in the aqueous dispersion prior to or during foaming. Alternatively, the beneficial agent may be incorporated in the gelled foam by, for example, immersing the gelled foam in or spraying the gelled foam with a liquid, such as water, that contains the beneficial agent. Beneficial agents include, for example, pharmaceutical actives such as antimicrobial agents, non-steroidal anti-inflammatory agents, anti-tussives, decongestants, anti-histamines, expectorants, anti-diarrheals, histamine II receptor antagonists, H2 receptor antagonists (blockers), antacids, proton pump inhibitors, central nervous system agents, analgesics, antiparkinsonism drugs, narcotic analgesics, analgesics-antipyretics, antifungal agents, psychopharmacological drugs, and mixtures thereof.

Enzyme containing microspheres may be incorporated into the dried gelled foams by adding the microspheres before or during foam formation. The use of microspheres, such as disclosed in Prud'homme, U.S. Pat. No. 6,268,191, allows for the controlled release of agents which are otherwise not suitable for incorporation into the dried gelled foams.

Various formats of foams may used in the food, pharmaceutical, and personal care areas. In general, the foam may be the product itself, ready to use, apply or eat, or it may be a "dry version" of a product that after fast rehydration turns into the product. As an example a piece of foam containing surfactants, fragrance and other suitable actives may turn into a liquid shampoo after fast rehydration in the hand or in the hair of the consumer. Or a dry piece of foam containing edible food ingredients can turn in to a gelled piece of restructured food after rehydration in hot or cold water.

Edible dried gelled foams can be used as carriers for beneficial agents, for example, antibiotics, antibacterial agents, antifungal agents, and micronutrients, breath freshening agents, and vitamins such as vitamin A, minerals such as iron, and other food supplements. For dried gelled foams designed for human consumption, coloring, flavoring, sweeteners such as sugar, and other ingredients may also be added before, during, or after formation of the gelled foam.

A foam made with high calcium level (60-200% saturation), which contain containing drugs or pharmaceutical actives, can function as a non-dissolving pharmaceutical dosage form. They can be hydrated either in the oral cavity or prehydrated in water before ingesting it. Either way the dried gelled foam will be hydrated into to a gel or jelly like format. This can be swallowed with or without chewing. The gel like texture would be beneficial for individuals or for animals that have problems taking dry oral dosage forms such as tablets, capsules or similar, such as children, the elderly, individuals with little saliva secretions, or animals such as pets, for example cats, or farm animals.

The dried gelled foam may used to encapsulate fresh or dried foods, such as nuts, fruits, vegetables, and proteins. The foods are typically finely divided, such that the resulting dried gelled foam appears to be a homogeneous material. Foods that are sold as dehydrated materials are especially useful for this application. The food may be cooked prior to being incorporated into the foam. The fresh foods may be dried during the drying process. Typically foods include, for example, nuts, such a walnuts, pecans, and almonds; vegetables, such as carrots, peas, beets, tomatoes, celery, green beans, corn, turnips, potatoes, onions, and peppers; fruits, such as apples, peaches, pears, plumbs, apricots, pineapple, cherries, cranberries, raisins, and citrus fruits such as oranges, grapefruit, lemons, limes, tangerines, and cumquats; and proteins, such as soy protein and casein. Mixtures of various foods may be used. For dried gelled foams designed for human consumption, colors, flavors, sweeteners such as sugar, and other ingredients may also be added before, during, or after formation of the gelled foam. The dried gelled foam may comprise up to about 80 wt % of the food, based on the weight of the food containing dried gelled foam. Although there is no lower limit on the amount of food that may be present, when food is present, the dried gelled foam will typically comprise at least about 5 wt %, more typically at least about 10 wt % of food. The pH of a food containing dried gelled foam may be from near neutral (about pH 7.0) up to about 2.0, typically up to about 3.0.

As a food ingredient, dried gelled foams may be used as inclusions in breakfast cereals. The dried, gelled foam pieces will upon hydration gain a predetermined shape, and they may act as pop-up figures like rings, cubes, stars, and hearts, and more sophisticated figures like animals and cartoons. An edible dried foam may also be used as artificial croutons and bread pieces for soups, ingredients in dry mix meals like artificial berries and fruit pieces, as confectionery figures, and as confectionery strips and pads or marshmallow-like products.

Other food applications of foams may be products similar to bread, croutons or biscotti, foam as a format of dry food mixes made functional upon hydration and optionally mixing. Foams optionally flavored and or colored can be included in bakery products, dairy, ice cream, beverages and confectionary products. With a foam's given structure and compatibility properties, it has potentials in low carbohydrate products. Because the foams are non-toxic, edible, and having a entertaining swelling property in water, the foams are suitable as toys for children. The toys may or may not be intended to be eaten and, optionally, may have flavors, colors, fragrances or ingredients modifying texture or swelling properties included. Foams with the suitable ingredients can function as a instant drink product. A dose of foam is added to hot or cold liquid and upon stirring it will hydrate, disperse or dissolve and release flavors, colors, texture modifying or other ingredients that form the intended drink.

A foam made with low calcium levels (10-60% saturation) can function as a fast disintegrating or dissolving dosage form for delivery of beneficial agents and/or pharmaceutical actives to moist sites of the body such as the oral cavity, GI tract, nose and eye. To increase speed of dissolution it is recommended to use alginates with low molecular weight such as less than 150,000. Substances useful in dental hygiene that may be delivered, include, for example, fluorides, such as sodium monophosphate, sodium fluoride, and stannous fluoride; salts of active cations, such as silver, zinc, and potassium salts; chlorhexidine; triclosan; thymol; chloroxylenol; hexachlorophene; nascent oxygen generating agents, such as calcium peroxide; desensitizing agents, such as potassium nitrate, and abrasives, such as precipitated silica. Coloring, flavoring, sweeteners such as saccharin, and other ingredients may also be added.

Dried gelled foams are quickly hydrated when placed in the mouth and are suitable to stay in the mouth for prolonged periods of time as a denture support or to deliver beneficial agents such as those described above to the teeth and oral cavity, for varying times including overnight. Alternatively, if the gel-forming polymer is less than 100% saturated, for example only 10-60% saturated, dried gelled foams may be prepared that disintegrate when placed in the mouth.

The dried gelled foam may be used to form a physical barrier to prevent reflux into the esophagus. A predetermined amount of the dried gelled foam, or "dose," is used. In one method, the predetermined amount of the dried gelled foam is taken orally to serve as a physical barrier or "gastric raft" to prevent gastric fluids and/or bile acids from passing into the lower part of the esophagus.

In another method, a predetermined amount of alginate foam with an intermediate saturation (10-60%) is placed in the mouth where it hydrates and then partly dissolves and partly disintegrates before being swallowed. In the mouth foams with intermediate saturation are less sticky or tooth packing than alginate foams that only have sodium alginate (no calcium, no crosslinking) and do not dry the mouth as these foam often do. However, the dissolved and disintegrated alginate still has the ability to gel. For example, when this solution is dropped into a solution of calcium chloride, gel beads form. When the disintegrated and partly or completely dissolved alginate enters into the stomach, the acid will convert the alginate to an acid gel. If the composition contains an acid activated gelling agent, for example a calcium source such as calcium carbonate, the gelling ion will be released in the stomach and create a cross-linked alginate gel in the stomach. Carbonate salts will create gas in the gel resulting in a floating gel raft or "gastric raft," which can serve as a physical barrier to prevent reflux into the esophagus.

Calcium carbonate may be incorporated into the dried gelled foam during form formation by the use of an excess of calcium carbonate and a limited amount of pH modifier, for example, glucono delta-lactone (GDL), so that only part of the calcium carbonate present reactions with the pH modifier. Both the amount of calcium crosslinking and the extent to which the calcium carbonate present during gel formation react can be controlled by controlling the amount of pH modifier present during gel formation. Thus, it is possible to prepare foams containing a predetermined amount of calcium carbonate, which react in the stomach. Predetermined amounts of other ingredients, such as H2 antagonists such as cimetidine (TAGAMET®), famotidine (PEPCIDINE®), nizatidine (AXID®), and/or ranitidine (ZANTAC®), and/or proton pump inhibitors, such as rabeprazole (ACIPHEX®), lansoprazole (PREVACID®), omeprazole (PRILOSEC®), and/or pantoprazole (PROTONIX®), may also be incorporated into the dried gelled foam using the methods described herein so that a single dose that comprises both the gastric raft and the appropriate medication can be produced.

For certain oral care applications, an abrasive or polishing agent may be incorporated into the dried gelled foam. Suitable abrasives, or polishing agents, include finely divided water-insoluble powdered materials having no or very low water solubility, typically having a particle size of about 1 to 40 microns in diameter, more typically about 2 to 20 microns in diameter, with normal particle size distributions, and which do not affect formation of the dried gelled foam. These materials have polishing activity without being overly abrasive. Typical abrasives include: calcium-based polishing agents, such as dicalcium phosphate dihydrate (generally known as dicalcium phosphate), tricalcium phosphate, calcium pyrophosphate, calcium silicate, and calcium aluminate; sodium metaphosphate; amorphous silica; crystalline silica; precipitated silica; complex aluminosilicate; aluminum hydroxide; aluminosilicates, bentonite, talc, aluminum oxide, silica xerogels, and mixtures thereof. A suitable abrasive is non-colloidal silica, such as ZEODENT® 113 (J.M. Huber Co., Havre de Grace, Md. USA). Calcium carbonate may used as an abrasive. It may be incorporated into the dried gelled foam during form formation by the use of an excess of calcium carbonate and a limited amount of pH modifier so that only part of the calcium carbonate present undergoes reaction with the pH modifier. Flavors, fragrances, and/or colorants may also be added.

In addition to oral care and dental hygiene, the dried gelled foams are useful in other personal care applications, such as in the application of beneficial agents, such as cosmetic agents, to the hair and/or the skin. Water-disintegratable dried gelled foams that are soft and flexible prior to and during application are used. They provide sustained delivery of the ingredients to the desired site of application, during, for example a bath or shower, while also providing a slowly disintegrating substrate that mechanically delivers the ingredient to the hair or skin and partially or completely disintegrating and washing away during application.

The dried gelled foam may used as a system for the delivery of a cosmetic agent, that is, a beneficial agent that produces a cosmetic effect when applied to human skin and/or hair. Cosmetic agents include for example, water, emollients; occlusive agents; moisturizers; humectants; sunscreen agents; self-tanning agents such as dihydroxyacetone; agents that remove hair (depilatories), such as mercaptans, especially salts of thioglycolic acid, such as calcium thioglycolate; exfoliating agents, for example, alpha- and beta-hydroxy acids such as lactic acid and glycolic acid, benzoyl peroxide, resorcinol, proteolytic enzymes, retinol and other similar compounds capable of causing desquamation of outer skin layers, microcrystalline cellulose; and the like. Occlusive agents, such as mineral oil, physically prevent or reduce moisture loss from the skin by formation of a water-impenetrable barrier over the stratum corneum. Humectants and moisturizers attract and hold water to the outside surface and upper layers of the *stratum corneum*. (*Stratum corneum* refers to the outer exposed layer of the epidermis). Emollients provide a softening or soothing effect on the skin surface and help control the rate of water evaporation and the tackiness of the composition.

Typically, the water-soluble plasticizer or plasticizers in the dried gelled foam, for example, glycerin, polyethylene glycol, polypropylene glycol, sorbitol, and PEG-4, are suitable humectants. Typical emollients are, for example, hyaluronan, lanolin oil; coconut oil; cocoa butter; olive oil; jojoba oils; castor oil; esters such as diisopropyl adipate, hydroxybenzoate esters such as $C_9$-$C_{15}$ benzoate, $C_{12-15}$ alkyl benzoate, iso-nonyl iso-nanoate diocyl adipate, octyl stearate, hexyl laurate, coco-caprylate, cetaryl isononanoate, isopropyl myristate, propylene glycol dicaprylate/dicaprate, octyldodecyl neopentanoate and propylene glycol isoceteth-3 acetate, decyl oleate, and caprylic/capric triglycerides; cyclomethicone; dimethcone; phenyltrimethicone; alkanes such as mineral oil, silicones such as dimethyl polysiloxane, and ethers such as dicapryl ether; polyoxypropylene butyl ethers, and polyoxypropylene cetyl ethers.

Other cosmetic agents that may be delivered, include, for example, colored pigments and pigments that reflect, scatter, and/or absorb ultraviolet radiation, sometimes referred to as physical sunscreen agents or inorganic sunscreen, such as microfine surface treated titanium dioxide and microfine untreated and surface treated zinc oxide. Titanium dioxide may have an anatase, rutile, or amorphous structure and preferably has a mean primary particle size of between 5 nm and 150 nm, preferably between 10 nm and 100 nm, and more preferably between 15 nm and 75 nm. Zinc oxide preferably has a mean primary particle size of between 5 nm and 150 nm, preferably between 10 nm and 100 nm, and more preferably between 15 and 75 nm. Organic materials that absorb ultraviolet radiation, referred to as organic sunscreen agents, that may be delivered to the skin by the dried gelled foam include, for example, p-aminobenzoic acid (PABA); benzophenone-1 (2,4-dihydroxybenzophenone); benzophenone-2 (2,2',4,4'-tetrahydroxybenzophenone); benzophenone-3 (2-hydroxy-4-methoxybenzophenone); benzophenone-4 (2-hydroxy-4-methoxybenzophenone-5-sulfoninc acid); benzophenone-6 (2,2'-dihydroxy-4,4'-dimethoxybenzophenone); benzophenone-8 (2,2'-dihydroxy-4-methoxy-benzophenone), benzophenone-12 (2-hydroxy-4-n-octoxy benzophenone); methoxycinnamate; ethyl dihydroxypropyl-PABA; glyceryl PABA; homosalate (homomenthyl salicylate); meradimate (menthyl anthranilate); octocrylene (2-ethylhexyl-2-cyano-3,3-diphenylacrylate); octyl dimethyl PABA; octinoxate (octyl methoxycinnamate); octisalate (octyl salicylate); avobenzone (4-t-butyl-4'-methoxy-dibenzoylmethane); ensulizone (2-phenylbenzimidazole-5-sulphonic acid); trolamine salicylate (triethanolamine salicylate); 3-(4-methylbenzylidene)-camphor; red petrolatum; and mixtures thereof.

Other cosmetic agents, such as waterproofing agents, preservatives, antioxidants, perfumes, colorants, plant extracts, absorbents, conditioners, anti-microbial agents, insecticides, pH adjusters, preservatives, and fragrances may also be applied in this fashion. Waterproofing agents include, for example, compounds that form polymeric films such as the $C_{30}$-$C_{38}$ olefin/isopropyl maleate/MA copolymer, dimethicone copolyol phosphate, diisostearoyl trimethylolpropane siloxysilicate, chitosan, dimethicone, polyethylene, PVP, and poly(vinylpyrrolidone/vinylacetate), etc. A preservative prevents microbial contamination and/or oxidation. Typical preservative/antioxidants are, for example, diazolidinyl urea, iodopropynyl butylcarbamate, vitamin E (alpha-tocopherol) and its derivatives including vitamin E acetate (alpha-tocopherol acetate), vitamin C (ascorbic acid), butylated hydroxytoluene (BHT), butylated hydroxyanisole (BHA), methylparaben, ethylparaben, n-propylparaben, and mixtures thereof. Cosmetic adjuncts include, for example, perfumes; and plant extracts such as Aloe vera, witch hazel, cucumber, etc. Surfactants, such as those listed above, may be used to aid in the removal of makeup, such as, for example, theatrical makeup. A useful surfactant for this purpose is sodium lauryl sulfate. Water, which may be considered an active that has a cooling, soothing, and moisturizing effect to the skin, may be delivered to the skin either by applying a wet foam to wet or dry skin, by applying a dry foam to wet skin, or by applying a dry foam to dry skin and hydrating the foam after application to the skin.

A convenient way of applying the cosmetic agent or agents to the face is with a facemask of dried gelled foam. The facemask may comprise a fast dissolving dried gelled foam so that it can be washed off after a predetermined time period. This would provide good cleansing, but the cosmetic agents might be removed from the skin when the facemask is washed off. If it is desirable not to remove the cosmetic agents from the skin, a slower dissolving dried gelled foam may be used. Then the facemask remains intact and can be peeled off or removed, preferably, in one piece. The facemask may be applied to a moistened face. This will provide the desired beneficial effect in addition to a cooling and soothing effect. To simplify addition of the mask may it be cut in smaller parts (one piece for the nose, one for the chin, etc). The stronger foams may be wetted before application. This makes it easier to get the mask fully hydrated. Suitable wet densities for the foam used in the facemask are 0.15-0.30 g/cm$^3$.

As described herein, wet integrity of the dried gelled foam may be controlled by the controlling calcium saturation (crosslinking), aeration time during the preparation of the dried gelled foam, type of alginate used to prepare the dried gelled foam (see, for example, the Table above), molecular weight of the alginate used to prepare the dried gelled foam, and thickness of the dried gelled foam. The integrity also depends on pore size. Foams made with smaller particle size of calcium carbonate gel more slowly, have less coalescence, and have smaller pores. These are generally stronger than foams produced with calcium carbonate of larger particle size and larger pore size. The flexibility of the dried gelled foam will also depend on molecular weight.

Foam may also have other cosmetic applications such as face or body wipes containing cosmetic agents or other beneficial agents for make-up removal or other cleaning purposes. These foams would typically be integral or slowly disintegrating upon hydration. When disintegrating, the end product could be flushed away with the wastewater. A foam containing abrasives, a solvent and optionally a moisturizer can be used as nail polish remover. A piece of foam containing the suitable actives could function as a single dose of products such as shampoo, hair styling gel or foam bath. Such products are normally water-based and supplied in tubes or bottles. A foam-based format would be easy to dose, lighter, better suited for transport and travels, and would not have the risk of leakage. Colorants, i.e., dyes and/or pigments, deposited on the foam surface can be transferred to the skin/body parts on wetting to create a "temporary tattoo." The foam patch can further dissolve providing cleansing or other cosmetic benefits. Alternatively, the colorants deposited on the foam surface could be non transferable and used as, for example, an indicator or identifier, such as a brand logo or bar code. Anionic dyes that are electrostatically bound to the foam are particularly useful. Foams can also be used for cleaning or stripping furniture.

The advantageous properties of this invention can be observed by reference to the following examples, which illustrate but do not limit the invention.

EXAMPLES

Glossary

Calcium carbonate Eskal 500 (particle size, 5.2 µm), Eskal 300 (particle size, 1.9 µm), Eskal 50 (particle size, 3.3 µm), and Eskal 20 (KSL Staubtechnik, Launingen Germany)
Calcium carbonate SOCAL® P2 (particle size, 0.28 µm), SOCAL® 31 (particle size, 0.07 µm), SOCAL® 90A (particle size, 0.24 µm) (Solvay, Salin de Giraud, France)
Calcium carbonate Minimum purity 99% (21.1 µm particle size) (Merck, Darmstadt, Germany)
Carrageenan VISCARIN® TP-206 (FMC, Philadelphia, Pa., USA)
Carrageenan, iota Alcohol precipitated iota carrageenan, viscosity (1 wt % aqueous solution at 20° C.)=153 mPs
Chitosan Chitosan hydrochloride, $F_A$=0.05, 240 mPas (20° C., 1% solution) (FMC Biopolymer, Norway)
CMC Sodium carboxymethyl cellulose, viscosity (4% solids, 25° C.)=10 to 55 mPas (Aldrich, Milwaukee, Wis., USA)
CRT 15000PPA CMC Waolcel CRT 15000PPA (Wolff Cellulosics, Walsrode, Germany)
Fructose CORNSWEET® Fructose (Archer Daniels Midland Corn Processing Division, Decatur, Ill., USA)
GDL LYSACTONE® glucono delta-lactone; gluconic acid δ-lactone (Roquette, Alessandria, Italy)
Glycerin ANALAR® glycerin (BDH Laboratory Supples, Poole, England)
HPMC PHARMACOAT® 603; hydroxy propyl methyl cellulose, viscosity (2 wt % aqueous solution at 20° C.=3 mPs (Shin-Etsu Chemical, Tokyo, Japan)
Hyaluronan Sodium hyaluronate, $M_w$ 2000 kDa (Kibun Food Chemifa CO., Ltd, Tokyo, Japan)
MCC AVICEL® PH-101, Non colloidal microcrystalline cellulose powder having an average particle size of 50 to 100 microns (FMC, Philadelphia, Pa. USA)
Methyl Cellulose Metolose SM4 (Shin-Etsu Chemical, Tokyo, Japan)
Model Physiological Aqueous solution of 142 mM NaCl and 2.5 mM Fluid $CaCl_2$, pH=6.9
Pectin Genu LM102AS (Copenhagen Pectin Factory Ltd., Lille Skensved, Denmark)
PROTANAL® LFR 5/60 Sodium alginate, viscosity (1 wt % aqueous solution at 20° C.)=3.7 mPs, pH=6.95 (FMC, Philadelphia, Pa., USA)
PROTANAL® LF 10/60 Sodium alginate, viscosity (1 wt % aqueous solution at 20° C.)=33.4 mPs, pH=6.12 (FMC, Philadelphia, Pa., USA)
PROTANAL® LF 20/40 Sodium alginate, viscosity (1 wt % aqueous solution at 20° C.)=140 mPs, pH=6.32 (FMC, Philadelphia, Pa., USA)
PROTANAL® LF 200S Sodium alginate, viscosity (1 wt % aqueous solution at 20° C.)=302 mPs, pH=6.63 (FMC, Philadelphia, Pa., USA)
PROTANAL® SF 120 Sodium alginate, viscosity (1 wt % aqueous solution at 20° C.)=424 mPs, pH=6.79 (FMC, Philadelphia, Pa., USA)
PROTANAL® SF 200 Sodium alginate, viscosity (1 wt % aqueous solution at 20° C.)=316 mPs, pH=6.43 (FMC, Philadelphia, Pa., USA)
PROTANAL® TA-250 Triethanol amine alginate, viscosity (1 wt % aqueous solution at 20° C.)=197 mPs, pH=5.79 (FMC, Philadelphia, Pa., USA)
PVA Polyvinyl alcohol, Mw=30,000 g/mole (Sigma, St. Louis, USA)
PVP Polyvinylpyrrolidone K15, Mw ~10 000 g/mole (Aldrich Chemie, Steinberg, Germany)
Saccharin SYNCAL® sodium saccharin (PMC Specialties Group, Cincinnati, Ohio, USA)
Silica ZEODENT® 113 Silica (J.M. Huber, Havre de Grace, Md., USA)
SLS TAXAPON® CP-P95 sodium lauryl sulfate (Henkel Mexicana, Dehydag, Mexico)
Sorbitol A-625 Non-crystallizing sorbitol solution, NF, aqueous polyol solution, 70% sorbitol (SPI Polyols, New Castle, Del., USA)
Tutti Frutti Flavor Natural and artificial tutti frutti type flavor (Symrise, Teterboro, N.J., USA)
TWEEN® 20 Polysorbate 20; polyoxyethylene sorbitan monolaurate (Fluka Chemie GmbH, Steinheim, Switzerland)
XL-CMC AC-DI-SOL®, Croscarmellose sodium, NF, Ph. Eur (FMC, Philadelphia, Pa., USA)

Sample Preparation and Test Methods

Sample Preparation

Samples were prepared using the following standard procedure except where noted. An aqueous solution of alginate was prepared. Plasticizer, calcium carbonate and the foaming agent were added to the alginate solution and blended about one minute at medium speed with a Hobart mixer to ensure uniformity. A newly prepared aqueous solution of the pH modifier was added to the mixture and the resulting composition was further blended at high speed to incorporate air for one to 4 min dependent upon the desired plasticity and the air content of the resulting foam. About 400-450 $cm^3$ was formed from 200 g of wet foam. The wet foam was then transferred into TEFLON® resin coated molds (23 cm×23 cm×0.8 cm) and leveled across the top of mold using a straightedge to provide a consistent foam thickness. The foam was allowed to set uncovered for about 30 min at room temperature. Then the molds were placed in a forced air drying oven at 40° C. and dried overnight (16 hr). The dried foams were approximately 5 mm high.

Density

Wet foam density was determined from the weight of wet foam required to fill a 100 ml container. Dry foam density was determined from the weight and volume of a dried foam square approximately 5 cm by 5 cm.

Absorbency

Except where indicated, a 5 cm by 5 cm sample was cut from the dried foam and conditioned for at least 16 hours at 20° C. and 66% relative humidity. The foam was weighed (dry foam weight) and then placed in an open dish containing at least 40 times the foam weight of a model physiological fluid at 37° C. After 30±1 min contact with the fluid at 37° C., the foam sample was grasped using tweezers, lifted from the fluid, allowed to drain for 30±1 sec, and then weighed (wet foam weight). The absorbency (g/g) is calculated as the wet foam weight divided by the dry foam weight. For comparison purposes, absorbency has been calculated as the weight of fluid absorbed by a sample of dried gelled foam that is 100 $cm^2$ in area and 5 mm thick.

Integrity

Integrity is a measure of the wet strength of the gelled foam. Integrity was determined by grasping the wet foam by a corner with tweezers and lifting to from the fluid after the absorbency test. Integrity was rated on a scale of 0 to 4, with 4 being highest. When the gelled foam was rated 0, it fell apart when lifted with the tweezers.

Flexibility

Flexibility is a measure of the ability of the ability of the dried gelled foam to deform without cracking or breaking. Flexibility was determined subjectively by folding the dried gelled foam over on itself. Flexibility was rated on a scale of 0 to 4, with 4 being the most flexible. When the dried gelled foam was rated 0, it was brittle and broke when bent.

Example 1

This example illustrates preparation of foams of different density, flexibility, and absorbency by varying the high speed blending time.

Following the general procedure, gelled foams containing 2% PROTANAL® SF 200 alginate, 10% glycerin, 0.3% $CaCO_3$ (Merck), 2% HPMC, 1.06% GDL, and the balance deionized water. Aeration time was varied as shown in Table 1. During preparation, approximately one third of the water added with the GDL mixture. The dried gelled foams were not preconditioned. Properties for the foams are shown in Table 1.

TABLE 1

Gelled foam density and absorbency as a function of blending time

| High Speed Blending Time (min) | Wet foam Density (g/cm³) | Dry foam Density (g/cm³) | Dry Foam Weight (g) | Absorbency (g/g) | Absorbency (g/100 cm²)[a] |
|---|---|---|---|---|---|
| 1.5 | 0.32 | 0.086 | 1.51 | 10.9 | 42 |
| 2.0 | 0.25 | 0.078 | 1.37 | 13.4 | 48 |
| 2.5 | 0.21 | 0.069 | 1.12 | 12.5 | 39 |
| 3.0 | 0.17 | 0.055 | 1.03 | 10.5 | 26 |
| 3.5 | 0.16 | 0.046 | 0.87 | 9.8 | 21 |

[a]Amount of fluid absorbed by 100 $cm^2$ of dried gelled foam 5 mm thick.

The absorbency of the foams was highly controlled by the blending time and the amount of aeration. A short blending time provided more compact foams than the softer and fluffier ones obtained after a longer time of aeration. The least aerated solution had the best properties connected to flow (i.e., the ability to pour the foamed solution into the mold as well as the smoothness of the foam surface after drying).

The force required to compress the dried gelled foams decreased as the density foam decreased. Dried gelled foams with lower density absorbed the liquid faster, while foams having even lower densities did not retain fluid as well, resulting in more fluid drainage from the foam when removed from the fluid. Although the dried gelled foams with somewhat higher densities had a slower absorption rate, their fluid binding capacities, reported as absorbency, are better. All the foams had acceptable integrity with little or no differences. The foams having the lowest densities were more transparent than the more compact foams, which contained some visible air bubbles after fluid absorption.

Example 2

This example illustrates modification of the foam integrity by adjusting the levels and ratio between calcium and alginate. Following the general procedure, gelled foams were prepared with 2% PROTANAL® SF200 alginate, 10% glycerin, 0.6% TWEEN® 20 and 2% HPMC using different calcium concentrations at a constant ratio of GDL and $CaCO_3$ (Merck). A Silverson mixer was used in place of the Hobart mixer. The procedure used the same order of ingredient addition as was used when a Hobart mixer was used, but with 4 min of high speed mixing. The first minute of high speed mixing after the GDL addition was without addition of air. To decrease the wet foam density, air was added using a subsurface air stream for 3 min while mixing. The dried gelled foams were not preconditioned before determination of absorbency.

An alternative absorbency test was used in which gelled foam discs about 1.2 cm in diameter were soaked in saline solution at room temperature. Results are presented in Table 2.

TABLE 2

Gelled foams with varying ratio of calcium and alginate

| | Sample | | | | |
|---|---|---|---|---|---|
| | 2-A | 2-B | 2-C | 2-D | 2-E |
| $CaCO_3$ | 0.60% | 0.30% | 0.23% | 0.23% | 0.15% |
| GDL | 2.12% | 1.05% | 0.80% | 0.80% | 0.53% |
| % saturation | 200% | 100% | 75% | 75% | 50% |
| TWEEN ® 20 | Yes | Yes | Yes | No | Yes |
| Wet density (g/cm³) | 0.39 | 0.36 | 0.35 | 0.32 | 0.33 |
| Homogeneity | 4 | 4 | 3-4 | 3-4 | 1 |
| Dry density (g/cm³) | 0.09 | 0.09 | 0.10 | 0.05 to 0.09 | 0.02 |
| Flexibility | 2 | 3 | 4 | 3 | NT[a] |
| Absorbency (g/g) | | | | | |
| 5 min | 7.77 | 8.32 | 11.20 | 4.62 | 8.11 |
| 30 min | 7.45 | 10.45 | 10.87 | 11.64 | 8.29 |
| Integrity | 4 | 3-4 | 3 | 3-4 | 1 |

[a]NT = not tested.

It was found that 100% calcium saturation gave strong gelled foams and the best absorption properties. The integrity became poorer as the calcium saturation was reduced to 75%. However, a higher absorbency rate was observed for the 75% saturated foam. Use of 200% saturation gave more brittle compact foams with poorer absorbency capacity.

Gelled foams made with 100% calcium contents had sponge like properties and maintained the same properties even after lying in liquid for several weeks.

The gelled foams made with 50% calcium saturation using the Silverson mixer technique were inhomogeneous. However, uniform gelled foams were made at 50% calcium saturation using the Hobart mixer technique.

Example 3

This example illustrates preparation gelled foams with higher solids content using a lower molecular weight alginate. Gelled foams were prepared as in Example 2. The formulation used 3.6% PROTANAL® LF20/40 alginate, 10% glycerin, 0.6% TWEEN® 20, 2% HPMC, 0.41% CaCO$_3$ (Merck), 1.44% GDL with deionized water to 100%. Foams cast from wet foam with a density of 0.36 g/ml gave dry gelled foams with a density of 0.08 g/cm$^3$.

The dried gelled foams were not preconditioned. The alternative absorbency test was used in which gelled foam discs about 1.2 cm in diameter were soaked in saline solution at room temperature. Absorbency was 11.30 g/g after 30 sec and 12.07 g/g after 5 min. The gelled foams had excellent integrity with a rating of 4.

Example 4

Using the general procedure, gelled foams were prepared using a Hobart mixer and a basic formulation of 2% PROTANAL® SF120 alginate, 0.3% CaCO$_3$ (Merck), 1.060% GDL. Foams presented in Table 3 were tested for absorbency without pre-conditioning except for Example 4-3. "Absorbency (g/100 cm$^2$)" was calculated for a 5 mm thick sample of dried gelled foam.

TABLE 3

|  | 4-1 | 4-2 | 4-3 | 4-4$^a$ | 4-5 | 4-6 |
|---|---|---|---|---|---|---|
| TWEEN ® 20 | 0.6% | 0.6% | 0.5% | 0.3% | 0 | 0 |
| SF-120 | 2.0% | 2.0% | 0 | 0 | 0 | 0 |
| LF40/60 | 0 | 0 | 4.0% | 4.0% | 0 | 0 |
| TA-120 | 0 | 0 | 0 | 0 | 2.0% | 2.0% |
| HPMC | 1.5% | 1.0% | 1.5% | 1.5% | 1.5% | 1.5% |
| Wet density | 0.23 | 0.28 | 0.23 | 0.22 | 0.20 | 0.27 |
| Absorbency (g/g) | 9.5 | 11.2 | 11.0 | 11.3 | 10.9 | 13.3 |
| Absorbency (g/100 cm$^2$) | 44 | 55 | 67 | 63 | 44 | 71 |
| Sticky | Yes | Yes | Yes | No | No | NO$^b$ |

$^a$Preconditioned
$^b$Gelled foam had slightly less wet strength.

Several dried foams made using TWEEN® 20 had a sticky surface when touched. Example 4-4 made with a lower level of TWEEN® 20 was not sticky. Foams made with TWEEN® 20 had larger pores, which provided a fast absorbency but less retention. Foams made with PROTANAL® TA-250 alginate, a triethanol amine alginate, as in Examples 4-5 and 4-6 had slightly less wet strength.

Example 5

This example illustrates stabilization of the wet foam structure by HPMC. Foams were made using Hobart mixer as in Example 1, except that the amount of HPMC varied from 0.5% to 3.0%. Density and absorbency are shown in Table 4.

TABLE 4

Effect of HPMC content

| % HPMC | Density - wet foam (g/cm$^3$) | Density - dry foam (g/cm$^3$) | Absorbency (g/g) | Absorbency (g/100 cm$^2$)$^c$ |
|---|---|---|---|---|
| 0.5%$^a$ | 0.23 | 0.100 | 12.3 | 59 |
| 1.0%$^a$ | 0.33 | 0.100 | 10.3 | 46 |
|  | 0.26 | 0.092 | 12.4 | 52 |
|  | 0.22 | 0.075 | 11.9 | 41 |
|  | 0.21 | 0.066 | 12.2 | 37 |
|  | 0.18 | 0.062 | 10.4 | 29 |
| 1.5%$^b$ | 0.29 | 0.091 | 12.1 | 50 |
|  | 0.25 | 0.072 | 13.3 | 45 |
|  | 0.21 | 0.071 | 11.6 | 38 |
|  | 0.20 | 0.059 | 10.1 | 27 |
|  | 0.17 | 0.053 | 9.9 | 23 |
| 2.0%$^b$ | 0.32 | 0.086 | 10.9 | 42 |
|  | 0.25 | 0.078 | 13.4 | 48 |
|  | 0.21 | 0.069 | 12.5 | 39 |
|  | 0.17 | 0.055 | 10.5 | 26 |
|  | 0.16 | 0.046 | 9.8 | 21 |
| 3.0%$^a$ | 0.28 | 0.079 | 11.4 | 41 |

$^a$Preconditioned.
$^b$Not preconditioned.
$^c$Calculated for a 5 mm thick sample.

Foams containing 0.5% HPMC had somewhat greater collapse during drying compared to those prepared with higher concentrations of HPMC. The dried gelled foam containing 0.5% HPMC was as flexible as the others prepared with higher levels of HPMC (1.0%, 1.5%, 2.0%, and 2.5%) but did not fully recover the same shape after bending or compression. The dried gelled foam prepared with 3.0% HPMC required somewhat more force to compress. The absorbency of the dried gelled foam was only slightly dependent on the amount of HPMC.

Example 6

This example illustrates the pH when the pH modifier is added.

The pH of a composition containing PROTANAL® SF120 alginate (100.0 g, 4% aqueous solution), glycerin (16.0 g), deionized water (50.0 g), HPMC (3.0 g), CaCO$_3$ (0.6 g) (Merck) was 8.6. A freshly made solution of 2.12 g of GDL and 28.3 g of deionized water was added. The resulting composition was mixed with the Hobart mixer to produce a wet foam. Before gelling, the wet foam had a pH of 6.3.

Example 7

This example illustrates that varying the concentration of the plasticizer affects the flexibility and absorbency of the dried gelled foam.

Using the general procedure, dried gelled foams were prepared from compositions containing 2% PROTANAL® SF200, 0.3% CaCO$_3$ (Merck), 1.06% GDL, 1.5% HPMC, the amount of glycerin indicated in Table 5, and the balance deionized water. The blending time at high speed with the Hobart mixer was 2.5 min for all the foams. The gelled foams were dried overnight at 40° C.

Some dried gelled foam samples were tested the same day they were removed from the oven without pre-conditioning at 66% relative humidity. The remainder of the dried gelled foam samples were sealed in a MIMIGRIP® low density polyethylene bag. These foams had the same absorbency five days later as those tested on the first day.

Absorbency increased as the plasticizer concentration was lowered. The flexibility of the foams was acceptable. Decreasing the plasticizer gave a harder, less pliable foam, which required greater force to bend. A high concentration of glycerin, such as 150%, may give a sticky surface.

TABLE 5

Absorbency as a function of glycerin concentration

| Glycerin (%) | Density of the Wet Foam (g/ml) | Absorbency (g/g) | Absorbency (g/100 cm$^2$) |
|---|---|---|---|
| 7.0 | 0.25 | 16.6 | 48 |
| 8.5 | 0.26 | 15.3 | 51 |
| 10.0 | 0.25 | 13.3 | 45 |

Example 8

This example illustrates that varying the concentration of the plasticizer and adding an additional polymer affect the absorbency of the dried gelled foam.

Dried gelled foams were prepared using a formulation of 2% of the alginate shown in Table 6, 0.3% CaCO$_3$ (Merck), 1.06% GDL, and 1.50% HPMC. The materials shown in Table 6 were added to the formulations.

TABLE 6

| Materials Added | Alginate | Density wet foam (g/ml) | Absorbency (g/g) | Absorbency (g/100 cm$^2$)$^a$ |
|---|---|---|---|---|
| 0.5% CMC | SF 200 | 0.21 | 12.2 | 42 |
|  | SF 200 | 0.24 | 13.7 | 48 |
|  | SF 200 | 0.28 | 14.6$^b$ | 68 |
| 1.0% CMC | SF 200 | 0.25 | 13.5 | 53 |
| 10.0% glycerin | SF 200 | 0.30 | 13.6$^b$ | 59 |
| 1.0% CMC | SF 120 | 0.22 | 13.6 | 47 |
| 8.0% glycerin | SF 120 | 0.25 | 14.5 | 61 |
|  | SF 120 | 0.27 | 14.6 | 59 |
| 0.5% XL-CMC | SF 200 | 0.24 | 13.4 | 49 |
|  | SF 200 | 0.28 | 13.9$^b$ | 49 |
| 1.0% XL-CMC | SF 200 | 0.26 | 13.4 | 58 |
| 10.0% glycerin | SF 200 | 0.29 | 13.9$^b$ | 65 |
| 1.0% XL-CMC 8.0% glycerin 0.5% CMC | SF 120 | 0.26 | 14.7 | 67 |
| 0.5% XL-CMC 10.0% glycerin | SF 200 | 0.26 | 13.1 | 61 |
| 0.5% CMC | SF 120 | 0.26 | 14.1 | 59 |
| 0.5% XL-CMC 8.0% glycerin 1.0% CMC | SF 120 | 0.27 | 15.0 | 62 |
| 1.0% XL-CMC 10% glycerin | SF 120 | 0.26 | 13.1 | 63 |
| 7.0% glycerin | SF 200 | 0.26 | 16.6$^b$ | 48 |
| 8.5% glycerin | SF 200 | 0.25 | 15.3$^b$ | 51 |
| 8.0% glycerin | SF 120 | 0.21 | 12.6 | 38 |
|  | SF 120 | 0.23 | 14.0 | 45 |
|  | SF 120 | 0.23 | 13.1 | 49 |
|  | SF 120 | 0.26 | 13.5 | 51 |
| 10.0% glycerin | SF 200 | 0.21 | 11.6$^b$ | 38 |
|  | SF 120 | 0.22 | 10.4 | 43 |
|  | SF 200 | 0.25 | 13.3$^b$ | 45 |
|  | SF 200 | 0.29 | 12.1$^b$ | 50 |

$^a$Calculated for a 5 mm thick sample.
$^b$Not preconditioned.

Example 9

5 This example illustrates that varying the size of the CaCO$_3$ particles changes the gelling time and the degree of coalesce of air bubbles. Smaller particles have a higher surface area and, thus, release calcium ion faster.

Dried gelled foams were prepared from a composition containing 2% PROTANAL® SF200, 2% HPMC, 10% glycerin, 0.6% TWEEN® 20, and 0.3% calcium carbonate using the Silverson mixer. Foams were made using five different particle sizes ranging from a mean particle size of about 0.07 microns to 21.1 microns.

The particle size distribution of the of the 3.3 μm calcium carbonate particles and the 21.1 μm calcium carbonate particles was determined using a Beckman Coulter LS 130 laser diffraction instrument with the hazardous fluid module. The particle mixture in ethyl alcohol was sonicated for 8 sec to ensure particle dispersion prior to measurement. The particle size volume distribution was determined and the mean particle size calculated. The particle size supplied by the vendor was used for the other calcium carbonate particles.

The initial gelation time varied from less than 3 min to about 30 min after GDL addition, as judged by shaking the mold or gently touching the foam. The time to maximum gelation varied from 2.5 hours to greater than 16 hours, as determined for gel (not foam) compositions at 20° C. using a StressTech rheometer with a 2.35 g sample between serrated plates with a 1 mm gap at a frequency of 1 HZ and strain of 0.005

TABLE 7

| Particle size (μm) | Initial Gelation Time | Time at 20° C. to maximum gelling |
|---|---|---|
| 0.07$^a$ | <3 min after GDL addition | about 2.5 h |
| 0.24$^b$ | <3 min after GDL addition | about 3.5 h |
| 0.28$^c$ | <3 min after GDL addition | about 3.5 h |
| 3.3$^d$ | about 20 min after GDL addition | about 10 h |
| 21.1$^e$ | about 30 min after GDL addition | >16 h |

$^a$SOCAL ® 31, Solvay, Salin de Giraud, France
$^b$SOCAL ® 90A, Solvay, Salin de Giraud, France
$^c$SOCAL ® P2, Solvay, Salin de Giraud, France
$^d$Eskal 50, KSL Staubtechnik, Launingen, Germany
$^e$Merck, Darmstadt, Germany, minimum 99.0% purity Example 10

Foams were prepared using two different particle size calcium carbonates separately and in blends. The compositions are shown in Table 8.

When fine calcium carbonate particles (e.g., a mean particle size less than 1 micron) were used, the fine calcium carbonate was added and mixed for about 3.5 min at medium speed prior to the GDL addition. The foams made using CaCO$_3$ with finer particle sizes had smaller pores in the gelled foam, and absorbency decreased with pore size. Properties are shown in Table 8. Absorbency was measured using the test described in Example 2.

TABLE 8

|  | Ex 9-1 | Ex 9-2 | Ex 9-3 | Ex 9-4 |
|---|---|---|---|---|
| SF 200 Alginate | 2% | 2% | 2% | 2% |
| Glycerin | 10% | 10% | 10% | 10% |
| TWEEN ® 20 | 0.6% | 0.6% | 0.6% | 0.6% |
| HPMC | 2% | 2% | 2% | 2% |
| CaCO3 (0.28 μm) | 0.3% | 0.15% | 0.10% | 0 |
| CaCO3 (21.1 μm) | 0 | 0.15% | 0.20% | 0.3% |
| GDL | 1.06% | 1.06% | 1.06% | 1.06% |
| PROPERTIES |  |  |  |  |
| Wet density (g/cm$^3$) | 0.35 | 0.38 | 0.32 | 0.28 |
| Dry density (g/cm$^3$) | 0.057 | 0.06 | 0.05 | 0.05 |
| Pore sizes | Small 3 | Small-medium 3 | Medium 3 | Large 3 |
| Pore homogeneity |  |  |  |  |
| Softness/flexibility | 1-2/2 | 1-2/2 | 3/2 | 3/3 |

TABLE 8-continued

|  | Ex 9-1 | Ex 9-2 | Ex 9-3 | Ex 9-4 |
|---|---|---|---|---|
| Absorbency after 0.5 min | 2.9 g/g | 1.5 g/g | 4.2 g/g | 9.0 g/g |
| Absorbency after 5 min | 4.4 g/g | 2.3 g/g | 5.7 g/g | 10.0 g/g |
| Absorbency after 30 min | 5.6 g/g | 2.8 g/g | 8.8 g/g | 12.0 g/g |
| Integrity after saline | 4 | 4 | 4 | 3 |

Example 11

This example illustrates the absorbance of model physiological fluid as a function of time for a perforated and a non-perforated dried gelled foam.

Dried gelled foam was prepared as in Example 1 except that 8% glycerin and 1.5% HPMC were used. A blending time of 1 minute and 35 sec gave a wet foam density of 0.30 g/ml.

Dried gelled foam was cut into two 5 cm×5 cm samples with a dry density of 0.08 g/ml and a thickness of 6.5 mm. Using a needle, one of the foams was perforated with 150 holes evenly distributed. Each foam was soaked in the model physiological fluid. During the period of swelling the foams were regularly removed from the bath of model physiological fluid, weighed, and returned to the bath. Before weighing, they were lifted from the fluid with tweezers and allowed to drain for 15 sec. FIG. 1 shows that the perforated foam has a higher initial absorbency than the non-perforated foam.

Dried foam was saturated with the model physiological solution and cut with a razor blade lengthwise so an "envelope" was made. A pH-electrode was put into this envelope and the pH, measured without any air present, was 6.2.

A dry sample of the same foam was cut into small pieces with a pair of scissors (about 5-10 mm×1-2 mm). These were weighed. The absorbency was about 14 g of the model physiological solution per g of dried gelled foam. After a short while almost all of the liquid was absorbed and the pH of the mixture was measured as 6.2.

Example 12

This example shows that compressing the dried gelled foam does not reduce its absorbency.

Dried gelled foam was prepared as in Example 11 (wet density 0.27 g/ml). Eight 5 cm by 5 cm pieces were cut. Four pieces were compressed by placing the foam piece on the bench and adding a 5.0 kg weight on top of the individual pieces for 15 sec. The foam thickness and absorbency data comparing the compressed and uncompressed foams are in the following table

TABLE 9

Absorbency of compressed and non compressed foams

| Foam type | Thickness dry (mm) | Thickness swelled (mm) | Absorbency (g/g) |
|---|---|---|---|
| Non-compressed | 6.0-6.5 | 7.0-7.5 | 14.6 ± 0.4 |
| Compressed | 1-1.5 | 7.0-7.5 | 14.4 ± 0.2 |

Example 13

This example shows the used of the dried gelled foam in oral application.

A foam was prepared according to Example 1, except that 1.5% HPMC was used. The wet foam, having a wet foam density of 0.15 g/ml, was transferred into a 6 mm deep mold. The dried gelled foam was 3 mm thick.

Foam samples 1.5 cm by 5 cm were cut out and placed under the lip to cover the teeth and gum. The foam adhered and after approximately 3 to 5 min was fully hydrated. The foam had good integrity and showed no signs of disintegration or dissolution. The foam preparation is suitable to stay in the mouth for prolonged periods of time as a denture support or to deliver actives to the teeth and oral cavity, for varying times including overnight.

Example 14

A dried gelled foam was prepared as in Example 13, except that half the amount of $CaCO_3$ and GDL, corresponding to a 50% saturation of the alginate gelling sites, was used. A 1.5 cm by 2.5 cm piece was cut out of the 3 mm thick foam and applied to the mucosal roof of the oral cavity using the fingertip. The foam immediately stuck. During a period of 30-60 sec, the hydrating foam started to disintegrate and finally was released from the mucosa. The product continued to disintegrate and could be swallowed, expectorated or rinsed from the mouth. Ingredients such as flavors, sweeteners, actives, abrasives, foaming agents etc could be added be added to the foam for oral delivery or cleansing purposes.

Example 15

Dried gelled foam was prepared as in Example 1, except 0.5% HPMC and 8% glycerin were used. A 5 cm by 5 cm sample of the foam, which was about 7 to 7.5 mm thick, was swelled with the model physiological fluid. Two fold back clips (Connect, 31 mm wide) were attached on opposite sides of the foam. A plastic bag was attached to the one of the clips. Water was filled in the plastic bag until the foam started to break around the clip. The plastic bag and the clip were placed on a balance. The weight was 440 g. This indicates that these foams after swelling are very strong and have tensile strengths of at least 440 g.

Examples 16 and 17

A dried gelled foam was prepared with the following ingredients. All the ingredients were either food and/or pharmaceutical grade. 100 g of 4% solution of PROTANAL® SF 120 in water; 30 g of Sorbitol A-625; 5 g of HPMC; 0.45 g of $CaCO_3$ particles (SOCAL® P2); 1.59 g of GDL; 1 g of tutti frutti flavor; 2.1 g of a 2% saccharin solution; and 59.9 g of deionized water. The calcium ion in resulting dried gelled foam is sufficient to saturate 75% of the alginate.

All of the ingredients except the GDL and one third of the water were mixed using an ULTRA TURRAX® T25 basic (IKA-Werke) with a S25N-25G rotor/stator for 5 min at 11000 rpm and for an additional 5 min at 16000 rpm to disperse the calcium carbonate. The resulting dispersion was then further mixed for 10 min at high speed using the Hobart mixer to aerate. Freshly mixed GDL in the rest of the water was then added and mixing continued for 15 sec. Then the wet foam was transferred to a 4 mm deep mold. The mold was kept at room temperature for about 30 min and then placed in a forced air drying oven at 40° C. for 5 hr.

By the same procedure a dried gelled foam was prepared with the following ingredients: 100 g of 4% solution of PROTANAL® SF 120 alginate in water; 30 g of Sorbitol A-625; 5 g of HPMC; 0.6 g of $CaCO_3$ particles (SOCAL® P2); 2.12 g of GDL; 1 g of tutti frutti flavor; 2.1 g of a 20% saccharin solution; and 59.2 g of deionized water. The wet foam began to set within 3 min. The calcium ion in this dried gelled foam is sufficient to saturate 100% of the alginate.

Both of the resulting dried gelled foams have very good flexibility and integrity. These dried gelled foams adhere to teeth for prolonged periods with no signs of disintegration or dissolution.

Example 18

A dried gelled foam was prepared with the following ingredients. All the ingredients were either food and/or pharmaceutical grade. 100 g of 4% solution of PROTANAL® SF 120 alginate in water; 30 g of Sorbitol A-635; 5 g of HPMC; 0.18 g of $CaCO_3$ particles (SOCAL® P2); 0.64 g of GDL; 1 g of tutti frutti flavor; 2.1 g of a 2% saccharin solution; 1.4 g of precipitated silica; and 59.7 g of deionized water. The calcium ion in the resulting dried gelled foam is sufficient to saturate 30% of the alginate. The dried gelled foam was prepared as in Example 16 except that the mixing time with the Hobart mixer was 10 min before addition of the GDL and an additional 20 sec after GDL addition before the wet foam was transferred to the mold. The calcium ion in this foam is sufficient to saturate 30% of the alginate.

The precipitated silica used in this Example had a particle size of 13.0 μm, as measured by a Beckman Coulter LS 130 laser diffraction instrument with the hazardous fluid module. Prior to measurement, the silica particle mixture in ethyl alcohol was sonicated for 8 sec to ensure particle dispersion.

The wet foam density was 0.33 g/cm$^3$. The dried gelled foam was 1-2 mm in height. It had good flexibility and a dry foam density of about 0.13 g/cm$^3$. The dried gelled foam had greater strength than the more porous foam of Example 14. This dried gelled foam dissolves quickly in water. A 1.5 cm by 1.5 cm piece of dried gelled foam will dissolve in about 30 to about 60 sec when used as a tongue cleaner. A similar piece of dried gelled foam will partly disintegrate within 8 min when placed on the roof of the mouth.

Example 19

A dried gelled alginate foam was prepared with the following ingredients: 100 g of 4% solution PROTANAL® LF 20/40 alginate in deionized water, 14.3 g sorbitol SP, 3.0 g HPMC, 0.18 g calcium carbonate (Eskal 300), 0.64 g GDL, 1.17 g of a 8% aqueous saccharin solution, 2.0 g of precipitated silica, 2.0 g glycerin and 76.7 g deionized water. The calcium is sufficient to saturate 30% of the alginate. All the ingredients except the GDL and 10.0 g of the deionized water were mixed using a Silverson mixer for 2 min to disperse the calcium carbonate and silica and produce a homogeneous dispersion. Then the GDL was dissolved in the rest of the water and immediately added. The resulting reaction mixture was further mixed for 1.5 min using the Hobart mixer at high speed to aerate. The wet foam, with a density of 0.24 g/cm$^3$ was transferred to a 4 mm deep mold. The mold was kept at room temperature for about 30 min and then placed in a forced air-drying oven at 40° C. overnight. The resulting dried foam was 2 mm thick.

The water content of the dried gelled foam at ambient humidity was estimated to be about 10%. As shown in Example 20, when a dried gelled foam was equilibrated in a high humidity chamber, it had a water content of 11.6%. At ambient conditions the water content will slightly less than this value. The content of the foam is: alginate, 16.5%; HPMC, 12.3%; saccharin, 0.3%; sorbitol, 41.1%; glycerin, 8.2%; silica, 8.2%; GDL/Ca, 3.4%; and water, 10.0% (estimated, at ambient conditions). Tutti frutti liquid flavor (0.8 g) was sprayed using a pump sprayer on one surface of a 566 cm$^2$ piece of a 5 mm thick of the dried gelled foam. The liquid rapidly penetrated into the dried gelled foam, and the surface again appeared dry.

Example 20

Alginate foams were prepared as described in Example 19, except that PROTANAL® LF 10/60 alginate was used and the mixing time with the Silverson mixture before the GDL addition was 3 min. The resulting reaction mixture was aerated with the Hobart mixer for 35 sec. The resulting wet foam was transferred to a mold that 6 mm deep and had an area of 566 cm$^2$ and immediately, without gelation, dried in a forced air oven at 40° C. The composition of the wet and dried foams is shown in Table 10. The moisture content of 10% is estimated.

TABLE 10

| | Composition Before and After Drying | | | |
|---|---|---|---|---|
| Ingredient | Grams - wet foam | % - wet foam | Grams - dried foam | % - dried foam |
| Alginate | 4.0 | 2.29 | 4.00 | 5.25 |
| SLS | 1.41 | 0.81 | 1.41 | 1.86 |
| Silica | 22.64 | 12.94 | 22.64 | 29.73 |
| Saccharin | 0.85 | 0.49 | 0.85 | 1.12 |
| Sorbitol SP | 28.30 | 16.17 | 28.30 | 37.17 |
| Glycerin | 10.5 | 6.00 | 10.50 | 13.79 |
| $CaCO_3$ | 0.18 | 0.10 | 0.82 | 1.08 |
| GDL | 0.64 | 0.37 | | |
| Water from sorbitol | 12.13 | 6.93 | — | — |
| Water | 94.35 | 53.92 | 7.61 | 10.00$^a$ |
| Total | 175.00 | 100.00 | 76.13 | 100.00 |

$^a$Estimated, at ambient conditions.

About 0.8 g of tutti frutti flavor was sprayed on the dried foam and absorbed.

To determine the moisture content of the foam, a piece of the foam with the same composition was cut into pieces about 1 cm by 2 cm. The pieces placed in a humidity chamber for about 16 hours at 66% relative humidity and weighed. They were then dried at 105° C. for 20 hours and weighed. Calculated moisture content was 11.8%.

Example 21

This example illustrates a dried gelled foam containing carboxy methyl cellulose as a co-binder. The procedure of Example 20 was repeated except that the silica was first dispersed in water containing the saccharin and carboxy methyl cellulose was used as a co-binder. The alginate and carboxymethyl cellulose (Waolcel CRT 15000 PPA, Wolff Cellulosics) were dissolved in this suspension using a propeller mixer. To the resulting mixture were added the sorbitol, glycerol, calcium carbonate (Eskal 20), and SLS, and the resulting mixture mixed for 1 minute at medium speed with the Hobart mixer. A freshly prepared aqueous solution of the GDL was added. Aeration continued at high speed for 55 sec. The resulting wet foam was poured into a 6 mm deep mold with a volume of 340 cm$^3$ and dried in a forced air oven at 80° C. for 5 hours. The uncompressed thickness of the resulting dried gelled foam was 0.5 cm. The composition of the wet and dry foams is shown in Table 12.

TABLE 12

Composition Before and After Drying

| Ingredient | Grams - wet foam | % - wet foam | Grams - dried foam | % - dried foam |
|---|---|---|---|---|
| Alginate | 4.0 | 2.29 | 4.00 | 5.11 |
| CMC | 0.5 | 0.29 | 0.50 | 0.64 |
| SLS | 1.41 | 0.81 | 1.41 | 1.81 |
| Silica | 22.64 | 12.94 | 22.64 | 28.94 |
| Saccharin | 0.42 | 0.24 | 0.42 | 0.54 |
| Sorbitol | 28.30 | 16.17 | 28.30 | 36.18 |
| Glycerin | 12.3 | 7.03 | 12.3 | 15.73 |
| CaCO$_3$ | 0.18 | 0.10 | 0.82 | 1.05 |
| GDL | 0.64 | 0.37 | | |
| Water from sorbitol | 12.13 | 6.93 | 0.00 | 0.00 |
| Water | 92.48 | 52.85 | 7.82 | 10.00$^a$ |
| Total | 175.00 | 100.00 | 78.21 | 100.00 |

$^a$Estimated at ambient conditions.

The gelled foam of Example 21 is more flexible and stronger than the gelled foam produced in Example 20. Both foams disintegrate similarly in less than 1 minute when soaked in water. The foams may be compressed to less than half their uncompressed thickness and still retain the same properties of strength, flexibility and disintegration in water.

Example 22

This example illustrates a dried gelled foam containing carrageenan as a co-binder. The procedure of Example 21 was repeated except that carrageenan (VISCARIN® TP-206) was used in place of carboxymethyl cellulose and only half as much saccharin was used. To incorporate as much air as possible, mixing time with the Hobart mixer following addition of GDL was 1 min and 15 sec. No significant differences between the dried gelled foam formed in this example and the dried gelled foam formed in Example 21 were readily apparent.

Example 23

The procedure of Example 21 was repeated except that, before addition of the freshly prepared aqueous GDL solution, the reaction mixture was mixed at high speed for 2.5 min with a Silverson mixer. Then the freshly prepared aqueous GDL solution was added and mixing continued for another 0.5 min. The pores of the resulting dried gelled foam were smaller than those of the dried gelled foam produced in Example 21. The rate of hydration at the teeth was about the same as that of the foam produced in Example 21, but the foam absorbed salvia more slowly than of the foam produced in Example 21.

Example 24

This example illustrates a dried gelled foam containing methyl cellulose. Dried gelled foams were prepared according to the standard procedure from using 2% PROTANAL® SF120 alginate, 8% glycerin, 1.5% methyl cellulose, 0.3% calcium carbonate (Merck) and 1.06% GDL in water. The properties of the resulting dried gelled foams are shown in Table 13.

TABLE 13

Properties of Gelled Foams Containing Methyl Cellulose.

| Density - wet foam (g/cm$^3$) | Density - dry foam (g/cm$^3$) | Absorbency (g/g) | Absorbency (g/100 cm$^2$) |
|---|---|---|---|
| 0.19 | 0.088 | 11.7 | 47 |
| 0.24 | 0.093 | 11.6 | 49 |

The dried gelled foams had higher dry densities than the dried gelled foams prepared with hydroxy propyl methyl cellulose. The foam with wet density of 0.24 g/ml was not fully hydrated after 30 min in the model physiological fluid. In addition to a slower absorbency rate, the dried gel foam did not recover its original shape after compression as well as foams prepared with hydroxy propyl methyl cellulose.

Example 25

This example illustrates the preparation of a dried gelled foam containing hyaluronan. Dried gelled foams were made as described in the standard procedure with 2% PROTANAL® SF120 alginate, 1.0% solution of hyaluronan (added at end before the addition of GDL), 1.5% HPMC, 8% glycerin, 0.3% calcium carbonate (Merck) and 1.06% GDL. The concentration of hyaluronan in the dried gelled foam was 0.25%. The properties of the resulting foams are shown in Table 14.

TABLE 14

Properties of Gelled Foams Containing Hyaluronan

| Density- wet foam (g/cm$^3$) | Density- dry foam (g/cm$^3$) | Absorbency (g/g) | Absorbency (g/100 cm$^2$) |
|---|---|---|---|
| 0.17 | 0.046 | 13.9 | 30 |
| 0.28 | 0.073 | 15.6 | 54 |

These foams had less collapse during drying compared to foams that did not contain hyaluronan. Dried gelled foams containing hyaluronan were slightly softer against the skin than foams prepared without hyaluronan. When soaked in the physiological fluid, the hydrated hyaluronan containing foams were "slippery" due to release of dissolved hyaluronan.

Example 26

This example illustrates addition of a layer of chitosan to the foam. The foam was prepared as in Example 11, except that PROTANAL® SF120 was used as thee alginate and three times as much of GDL was used.

A solution of 2% chitosan and 5% glycerin was poured on the gelled foam before drying. The layer of solution was about 0.5-1 mm and it was not absorbed into the foam. After the foam was dried at 40° C. overnight, the film of chitosan was still visible on the surface, which was also sticky. However, the thin layer of chitosan does not affect the wet strength of the foam. The film of chitosan is still visible after keeping the foam in water.

Example 27

A dried gelled foam was prepared according to the procedure of Example 11, except that PROTANAL® LF200S alginate was used. The wet density of the foam after high speed mixing for 2 min with the Hobart mixer was 0.25 g/cm$^3$. The wet foam was poured in a mould with a depth of about 2 mm. As illustrated below, the dried foam was cut in the shape of a face with holes for eyes, mouth and nose. It was about 1.5 mm thick and weighed 0.013 g/cm$^2$.

The skin of the face was wetted, and the mask was applied. Additional water at about body temperature was added until the mask was fully hydrated. Upon hydrating the appearance of the mask changed from white to transparent. The mask was left on the face for 10 min and could now be removed entirely and in one piece. After removal of the mask, the skin was softer due to release of glycerin from the foam.

Example 28

This example illustrates a facemask containing hyaluronan. A facemask was prepared according to Example 27, except 0.20% hyaluronan was added to the composition. Mixing at high speed with the Hobart mixer for 1 min gave foam with a wet density of 0.30 g/cm$^3$. After drying, the dried gelled foam was about 1.5 mm thick and had a weight of 0.013 g/cm$^2$.

The mask was placed on the skin as in Example 27 and left for 10 min. The mask could not be removed in one piece, but could be removed in several smaller pieces or washed off. A viscous solution of hyaluronan was left on the skin and could be massaged into the skin after removal of the mask. The skin felt moist and soft after this treatment.

Example 29

This example illustrates a facemask containing microcrystalline cellulose. A facemask was prepared as Example 27, except that 7.50% MCC was used in place of some water and the alginate was 30% saturated. After the reaction mixture was mixed at high speed with the Hobart mixer for 2.7 min, a wet foam with a density of 0.28 g/cm$^3$ was produced. After drying, the resulting dried wet foam was about 1.5 mm thick and had a weight of 0.025 g/cm$^2$.

A facemask was prepared and placed on the skin in a similar manner as in Example 27. After 5 min the dissolved foam was massaged into the skin. The microcrystalline cellulose acted a peeling agent. The residue was removed with water. The skin felt moist and soft after this treatment.

Example 30

This example illustrates gel formation when partially disintegrated foam is added to an aqueous solution containing calcium ions. 140 mg dried gelled foam in which the alginate was 30% saturated was partly dissolved and partly dispersed in 2 g deionized water. Using a pipette, the suspension dripped into a solution of 0.1 M $CaCl_2$. Gel beads formed immediately.

The experiment was repeated with 190 mg dried gelled foam that was 50% saturated with calcium. The suspension was prepared with 4 g deionized water and dripped into the same solution of $CaCl_2$. Gel beads formed immediately. However, the gel beads formed from the 30% calcium saturated foam were stronger.

Example 31

This example shows the swelling of foams in milk and water. Dried gelled foams containing sugar have various food applications, such as inclusions and sweetening agents for breakfast cereal. They may also be used in beverages, such as coffee and tea.

(1) A dried gelled foam was prepared as described in Example 11 except that PROTANAL® SF 120 alginate was used. The blending time at high speed with the Hobart mixer was 1 min and 40 sec, producing a wet density of 0.27 g/cm$^3$. The resulting dried gelled foam was 0.65 cm thick and had a dry density of 0.071 g/cm$^3$. This foam is suitable for use as a wound dressing.

(2) Following the general procedure, a dried gelled foam containing 2% PROTANAL® LF200S alginate, 8% glycerin, 0.45% $CaCO_3$, 2% HPMC, 1.590% GDL, 0.220% saccharin, 3.9% fructose, 11.7% sucrose, 4.55% glucose and balance deionized water. The calcium was sufficient to saturate 150% of the alginate.

The sugars were added together with the HPMC and $CaCO_3$ before mixing. Mixing at high speed for 2.25 min gave a foam with wet density of 0.24 g/cm$^3$. The foam was pregelled for 30 min at room temperature before drying over night at 40° C. The dried gelled foam was 0.80 cm high with a dry density of 0.12 g/cm$^3$.

(3) To follow the swelling of the dried gelled foams in water and in milk, 2.0 cm by 2.5 cm piece of each foam cut out and weighed. A piece of each foam was soaked in water and another piece of each foam was soaked in milk. During the period of swelling, the pieces were regularly removed from the liquid, weighed, and returned to the liquid. Before weighing, each piece was lifted from the liquid with tweezers and allowed to drain for 15 sec.

Figure 2:
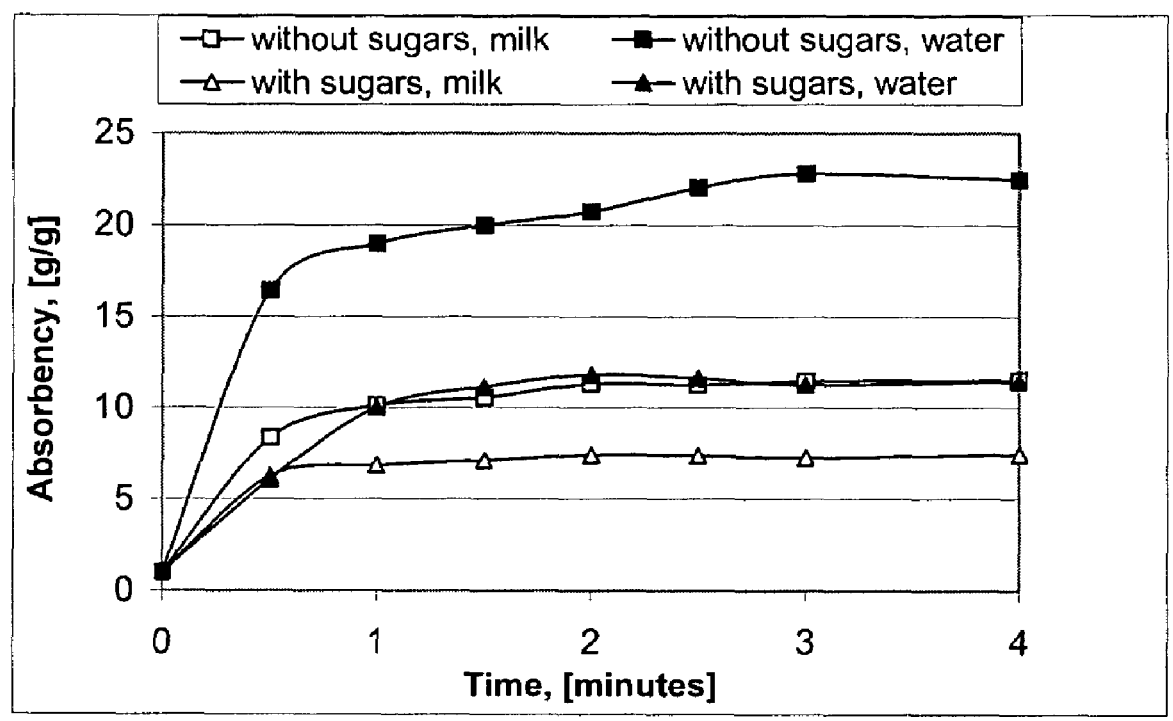
FIG. 2 shows the absorbency of milk and water for dried gelled foams with and without sugars.

FIG. 2 shows that the dried gelled foam without sugars absorbed more of each liquid than the dried gelled foam with the high content of sugars. Each foam absorbed more water than milk. The foam without sugar swelled in water so a thickness of 1.0 cm. The thickness of the other foams did not increase.

Both foams absorb the same amount of liquid when compressed (data not shown), but the foam with sugar has a slower absorbency rate. The texture of the foams swelled in milk is more brittle and more force has to be used to chew them. The brittleness/texture may be varied by rate of gelling by varying the particle size of $CaCO_3$ and also by increasing the saturation of calcium.

A foam with 20% sugar, prepared as described above, was made with calcium sufficient to saturate 100% of the alginate. However this foam dissolved in water. This was also somewhat weaker than the foam with 150% calcium saturation when swelled in milk.

Example 32

This example shows the absorbency of dried gelled foams with and without TWEEN® 20. Following the standard procedure, two dried gelled foams were prepared containing 2.5% PROTANAL® LF200S, 4% glycerin, 9% sorbitol (70%), 1.5% HPMC, 0.38% $CaCO_3$ (Merck), 1.33% GDL, and the balance deionized water. One foam comprised 0.03% TWEEN® 20 and the other did not. The TWEEN® 20 produced more coalescence. The dried gelled foams were about 3 mm thick and, as in Example 4, larger pores were observed in the TWEEN® 20 containing dried gelled foams compared to dried gelled foams that did not contain TWEEN® 20.

To measure the absorbency rate, 1 ml of model physiological solution was added to surface of the dried gelled foams with a pipette, and the time used to absorb all the liquid was measured. The time of absorbency at either surface of the foam containing TWEEN® was less than 1 second. Foams prepared without TWEEN® 20, but otherwise having an identical composition and the wet density typically, typically had an absorbency time of 6 to 12 sec for the top surface and 12 to 17 sec for the bottom surface (surface orientation reference is to as cast in the mold).

Microscopic examination of foams without TWEEN® 20 showed that the cells at the foam surface normally are closed, resulting in a complete film. However, for foams containing TWEEN® 20, some of the cells were open so the foam did not have continuous surface film.

Example 33

This example shows that silver salts can be incorporated in dried gelled foam and released to provide antibacterial effects. Dried gelled foams were prepared with TWEEN® 20, as in Example 32, except that varying concentrations of silver nitrate (Merck Darmstadt, Germany) or silver acetate (Fluka Chemie GmbH, Buchs, Switzerland) were added. The silver salts were dissolved in deionized water and added before the mixing step.

The dried gelled foams became brown when exposed to light after drying. The color intensity increased with increasing silver concentration, and the color was always homogeneously distributed. To measure the amount of ionic silver released from the foam when hydrated, an ion selective electrode was connected to an Orion EA 940 ion-meter (Thermo Orion, Beverly, Mass., and USA). A standard curve was prepared with solutions of known $AgNO_3$ concentrations. Two pieces of foam, approximately 2.5 cm by 2.5 cm were weighed and added to a mixture of 100.0 g deionized water and 2.0 ml ISA (Ion Strength Adjustor 94011, aqueous solution of $NaNO_3$) with continuous stirring. Table 15 shows silver released when the foam was hydrated as a function of silver concentrations in the foam. The calculation of silver concentration in the foam is based on an assumption of 16% moisture content in the dried foams.

TABLE 15

Release of Ionic Silver from Dried Gelled Foam after Rehydration

| Silver source used in foam preparation | Silver added, [%] (wet) | Silver added, [%] (dry) | Silver measured, [%] | Silver released, [%] |
|---|---|---|---|---|
| $AgNO_3$* | 0.08 | 0.28 | 0.110 | 33 ± 1 |
| $AgNO_3$ | 0.04 | 0.14 | 0.026 | 19 |
| $AgNO_3$ | 0.02 | 0.07 | 0.022 | 31 |
| $AgC_2H_3O_2$ | 0.02 | 0.07 | 0.029 | 42 |

*Average of three measurements. Other values are a single measurement.

To confirm antimicrobial effect and release of ionic silver, the well-known bacteria occurring in wounds, *Staphylococcus aureus*, was used. 100 µl of this bacteria suspended in saline was plated on a Tryptone Soya agar plate (Oxoid Ltd., Basingstoke, Hampshire, UK).

A piece of foam, 1 cm by 1 cm, was then placed on the plate which was then covered and incubated at 30° C. A clear zone of inhibited growth could be seen around the foam the following day. A piece of foam made according to Example 32, which did not contain silver, was placed on the same plate as a control. No bacterial growth inhibition was seen round or under the foam.

Example 34

This example shows incorporation of chitosan into dried gelled foam. Dried gelled foams with TWEEN® 20 were prepared as in Example 32, except that 0.5% chitosan ($F_A$=0.47) was added as an 8% solution in deionized water. ($F_A$ is the mole fraction of acetylated amino groups.) The solution was added during mixing at high speed 45 sec after addition of GDL. Mixing was continued for another 2.5 min, producing a foam with a wet density of 0.26 g/ml. The foam appeared relatively homogeneous at this low concentration of chitosan and had the same properties of wet strength and absorbency as foams that did not contain chitosan.

Foams could also be prepared with 1.0% chitosan addition, but chitosan-alginate precipitates were visible in the dried foam, and it was not possible to incorporate as much air as usual. A wet foam density of 0.38 g/ml was obtained after 3 min of high speed mixing.

Example 35

This example shows that foams with chitosan have antibacterial properties. A piece of foam from Example 34 was evaluated for antibacterial properties as in Example 33 except that the foam was soaked in saline solution before it was placed on the agar plate. After one day of incubation at 30° C. no growth of bacteria was visible between the foam piece and the agar.

A dried gelled foam was coated with a chitosan chloride as described in Example 26, except that the chitosan solution used to coat the foam was a 4% solution of chitosan chloride ($F_A$=0.47) with 5% of glycerin. The dry foam piece was placed at an agar plate with 300 µl bacteria suspension to increase foam hydration. After one day of incubation at 30° C. no growth of bacteria was visible between the foam piece and the agar. Although, foam had clear bacteriostatic effects in the area that was in direct contact with the foam, a clear (i.e., bacteria-free) zone surrounding the test sample was not observed. Chitosan is strongly bound to the alginate and is not released from the foam. A piece of foam made according to Example 32, which did not contain chitosan, was placed on the same plate as a control. No bacterial growth inhibition was seen round or under the foam. A droplet of 8% solution of the same chitosan dropped on the agar plate confirmed the general antibacterial effect of chitosan.

Example 36

This example shows foam dried using infrared drying. Wet foam was made as in Example 32, but molded in trays made for a Mettler Toledo HR73 Halogen Moisture Analyzer infrared drying apparatus (diameter: 9.5 cm, height: 0.5 cm). TEFLON® foils (BYTAC®) were added to the bottom of the trays. After 10 min of drying at a setting of 100° C., 20% of the water had evaporated from the cast foam, and the foam has sufficient integrity to be turned over to continue drying on the other surface. After 5 min of additional drying, another 20% of the water had been removed. The strength of the foam was sufficient for further drying, e.g. on heated rolls like drying of paper.

Example 37

This example shows how the drying temperature and temperature profile affects the resulting wet strength of the foam as determined by tensile strength measurements. It was desired to minimize the processing time while maintaining wet strength.

Three foam samples were made with a wet density (0.19 g/ml) and height as described in the standard procedure. The composition was 2.5% PROTANAL LF200S, 8.0% glycerin, 1.5% HPMC, 0.38% CaCO₃ (Merck), 1.330% GDL and the balance deionized water. The cast foams were allowed to stand at ambient temperature on the laboratory bench for 30 min prior to hot air drying. One foam was dried at 40° C., one at 60° C., and one at 80° C.

The wet integrity of each foam was tested with a SMS Texture Analyzer and A/TG tensile grips. The test speed was set to be 0.5 mm/s. The dried foams were soaked in the model physiological solution and kept in the solution until fully hydrated. Before the foam was tested, most of the solution was gently squeezed out by placing the foam between a few sheets of paper and pressing lightly with the hands. The wet foam was about 2-3 mm thick. A scalpel was used to cut the foam in a bone-shape and the piece was fastened to the tensile grips of the analyzer. The pieces were 5 cm long, 3.4 cm wide at the ends, and 2.4 cm wide at the center. The foam was cut in this shape to ensure breakage in the middle of the foam and not where it was attached to the grips. Approximate 0.5 cm of each end of the foam piece was used to fasten it to the grips.

The force used to stretch the foam was measured as a function of time, and maximum value before breakage was read. Table 16 shows the maximum values of tensile strength (±1 standard deviation from mean for five samples tested) for the three different foams. Statistical analysis based on t-test assuming equal variances (confidence interval=99%) indicates that the foams differ in wet strength.

TABLE 16

Maximum Wet Tensile Strength for Foams Dried at Varying Temperatures.

| Drying temperature (° C.) | Wet Tensile strength (g) |
|---|---|
| 40 | 281 ± 17 |
| 60 | 220 ± 21 |
| 80 | 175 ± 13 |

Additional dried gelled foams were prepared with the same composition but with a wet density of 0.25 g/ml and processed with varying time and temperature conditions for drying. One hour at 40° C., when combined with high temperatures in the later drying stage, was sufficient to obtain a faster drying time while maintaining a desired maximum tensile wet strength of the final foam. This data is shown in Table 17. Statistical analysis based on t-test assuming equal variances (confidence interval=99%) indicates that these foams do not differ in wet strength.

TABLE 17

Wet tensile strength of foam with drying temperature profiles

| | Drying temperature | | | Tensile strength (g) |
|---|---|---|---|---|
| | 40° C. | 60° C. | 80° C. | |
| Foam 1 | 4 hours | 2 hours | 1 hour | 331 ± 25 |
| Foam 2 | 3 hours | 2 hours | 1 hour | 354 ± 22 |
| Foam 3 | 2 hours | 2 hours | 1 hour | 371 ± 20 |
| Foam 4 | 1 hours | 2 hours | 1 hour | 352 ± 31 |

Example 38

This example shows foams suitable for use as a dentifrice. A dried gelled foam was prepared with the following ingredients: 50 g of 8% solution PROTANAL® LFR 5/60, 12.3 g glycerin, 40.3 g sorbitol SP, 0.5 g HPMC, 0.18 g CaCO₃, 0.64 g GDL, 1.5 g CRT 15000PPA CMC, 2.06 g of an 8% aqueous solution of saccharin, 22.64 g silica, 0.8 g PVP, 1.41 g SLS and 42.7 g deionized water. The calcium added was sufficient to saturate 30% of the alginate. All the ingredients were mixed with the Silverson mixer for 4 min and filled the mold of 340 cm³. The foam was immediately dried at 60° C. overnight. 7.5 mg of natural and artificial watermelon type flavor (Symrise, Teterboro, N.J., USA) (per dose, 4 cm by 0.5 cm of foam) was brushed on with a paintbrush and dried. A strong and flexible foam piece of 4 cm by 0.5 cm adhered well to the teeth. After 30 sec it was fully hydrated with saliva and brushing could begin. A second dried gelled foam was made using the same composition except that PVP was replaced with PVA, the calcium carbonate added was sufficient to saturate 20% of the alginate, and 0.3 g of a 0.005 g/ml aqueous solution of red coloring (Color K7057 D&C RED # 33, LCW Inc., South Plainfield, N.J., USA) was added before mixing. The resulting foam was pink. The other properties and performance of this foam were the same as the first dentifrice foam.

Example 39

This example shows a dried gelled foam for fast oral dissolution, which gives pleasant mouthfeel without stickiness or excessive viscosity in the mouth.

A dried gelled foam was prepared from 50 g of a 4% aqueous solution of PROTANAL® LFR5/60, 25 g sorbitol SP, 2.0 g XL-CMC, 3.0 g HPMC, 0.18 g CaCO₃ (Eskal 300), 0.64 g GDL, 2.0 g CRT 15000PPA CMC and 117.2 g deionized water. The calcium added was sufficient to saturate 30% of the alginate. The solution was mixed until homogeneous, about 3 min, with a Silverson mixer. Then the foam was further mixed for 1 min with a Hobart mixer giving a wet density of 0.18 g/ml. The foam was spread in two molds, which were about 3 mm high, and dried overnight, one at 40° C. and one at 60° C. The pores in the foam dried at 40° C. were larger than the pores in the foam dried at 60° C. Both foams were strong although somewhat brittle.

Example 40

This example shows formation of foam beads by precipitation of alginate in alcohol. Wet foam was prepared as described in Example 32. The wet foam was put into a plastic bag, and the bottom corner was cut forming a hole with a diameter of about 1 cm. The wet foam was pressed out through the hole and cut it into pieces of about 1.0 to 1.5 cm in length. The pieces were dropped into a stirred bath containing 4% glycerin and 9% sorbitol in ethanol. Round shaped beans formed. Dried beads, which remained in the bath a longer time before being removed, were more water-soluble, due to precipitation of the alginate rather than formation of crosslinks between the alginate molecules.

Example 41

This example shows a way of making a foam-based reconstitutable dosage form. A model active (titanium dioxide) was incorporated into a dried gelled foam, which upon moderate agitation will hydrate and disperse and suspend the model active in a free flowing, drinkable liquid.

A dried gelled foam was made containing 100.0 g of a 4% aqueous solution of PROTANAL® LF200S, 28.0 g sorbitol SP, 12.0 g glycerin, 3.0 g HPMC, 0.18 g CaCO₃, 0.64 g GDL, 31.4 g titanium dioxide, 0.04 g TWEEN® 20 and 24.7 g deionized water. The calcium added was sufficient to saturate 30% of the alginate. All ingredients were mixed at medium speed with a Hobart mixer for 1 min and then at high speed for 2.5 min. The resulting foam has a volume 340 cm$^3$, and it was immediately dried over night at 50° C. The resulting dried gelled foam was strong, soft and pliable with 8% moisture content. Two 1.5 cm by 3 cm pieces of foam dispersed when they were put into 100 ml deionized water and shaken for 1 minute to give a suspension of 0.5 g titanium dioxide/100 ml. The suspension remained stable for at least 5 min without sedimentation.

Example 42

This example illustrates a bi-layer dried gelled alginate foam. Foams were prepared with and without TWEEN® 20, as described in Example 32. The foam without TWEEN® 20 included 0.15% of an aqueous solution of 0.005 g/ml of coloring material, added before foaming. The foam without TWEEN® 20 was cast and dried. The wet foam containing the TWEEN® 20 was then cast directly on top of the dried gelled foam without TWEEN® 20 and dried. The two foam layers in the dried gelled foam structure were firmly attached and remained adherent after one day storage in tap water. Over time, the water-soluble coloring material was released from the foam into the water. The pore size and structure of the dried gelled foam surfaces were visibly different, and the absorption properties of the individual layers remained distinct. The layer which contained the TWEEN® 20 absorbed water immediately when water was placed on its surface. The layer without TWEEN® 20 required about 5 sec to absorb a droplet of water deposited on its surface.

Example 43

This example illustrates a dried gelled foam in which pectin is the gelling agent. A 200 g batch of a wet foam was prepared containing 2% pectin, 3.5% glycerin, 9 g % sorbitol SP, 1.5% HPMC, 0.2% CaCO$_3$ (Eskal 500), 0.7% GDL, 1% CMC (Walsrode CR$_T$ 15000) and the balance deionized water. There is 80 mg of calcium ion per g of pectin. First 133.4 g of an aqueous solution of 3% pectin, plasticizers, dry ingredients (except GDL) and two thirds of the water were blended using the Silverson mixer. Then a freshly made solution of GDL, and the remaining water was added. Mixing was continued at high speed with the Hobart mixer for 1.25 minutes. The resulting wet foam had a density of 0.21 g/ml. The wet foam was cast in a mold with 0.8 cm height and kept uncovered on the laboratory bench for 30 min and then dried over night at 40° C. The resulting dried gelled foam was 0.7 cm high, soft and pliable. When the dried gelled foam was transferred to water, it swelled and gave a weak gel.

Example 44

This example illustrates a dried gelled foam in which iota carrageenan is the gelling agent. A 200 g batch of wet foam was prepared containing 1.5% iota carrageenan, 3% glycerin, 9% sorbitol SP, 1.5% HPMC, 0.230% CaCO$_3$ (Eskal 500), 0.79% GDL, and the balance deionized water. The calcium ion present is 6 wt % of the iota carrageenan present. First 150 g of an aqueous solution of 2% iota carrageenan, plasticizers, HPMC and CaCO$_3$ were blended until homogeneity using the Silverson mixer. Then mixing was continued at high speed with the Silverson mixer for 1 min before a freshly made solution of GDL and the remaining water was added. The mixing continued for 15 sec and the resulting wet foam was cast in a 0.8 cm high mold. The wet foam had a density of 0.20 g/ml. The wet foam was cast in a mold with 0.8 cm height and kept uncovered on the laboratory bench for 30 min and then dried over night at 40° C. The resulting dried gelled foam was 0.6 cm high. When the dried gelled foam was transferred to water, it swelled and gave a weak gel.

A comparative foam was made using the same ingredients and formulation except that the CaCO$_3$ and GDL were omitted. The wet foam had a density of 0.20 g/ml. The wet foam was cast in a mold with 0.8 cm height and kept uncovered on the laboratory bench for 30 min and then dried over night at 40° C. The resulting comparative dried foam had larger pores, and the foam height was only 0.4 cm compared to 0.6 cm for the foam prepared with CaCO$_3$ and GDL. It was apparent that more coalescence occurred in the comparative foam during drying. When the comparative dried foam was left in tap water, it did not swell. It hydrated slowly and then dissolved.

Example 45

This example shows that pore size and gelling rate affect the wet strength of the foam. Four foams were prepared according to the standard procedure. The composition was 2.5% PROTANAL® LF200S, 3.0% glycerin, 9.0% Sorbitol SP, 0.03% TWEEN® 20, 1.5% HPMC, 0.48% CaCO$_3$ (as shown in Table 18), 1.37% GDL, and the balance deionized water. The calcium added was sufficient to saturate 125% of the alginate. Each batch of wet foam was divided and cast into four trays (7 mm high). The 4 wet; foams from each batch were kept uncovered at the laboratory bench at ambient temperature for 0, 20, 40, or 60 min, and then transferred to an air forced drying oven at 80° C. and dried for between 4 to 5 hr, depending on the time the sample was kept at the laboratory bench. The foam kept 0 min on the laboratory bench was dried 5 hr and the foam kept 60 min on the laboratory bench was dried for 4 hr. The drying temperature was decreased to 35° C. during about 4 hr and held kept at this temperature for about 7 hr.

Foams that were immediately dried at 80° C. had smaller pores than those kept at the laboratory bench for some time before drying. The foams prepared with Merck and Eskal 20 CaCO$_3$ had visibly different pore sizes between the 4 different gelling times. More coalescence was observed for the foams made with the largest CaCO$_3$ particles for time on the laboratory bench. Dry foam density was determined, but any variance due to time on the laboratory bench was difficult to measure with these thin foams using a hand calipers. The Eskal 500 foams were somewhat less pliable, but were the softest against the skin. Within each sample group, the foams with the smallest pores were the softest.

Dried foams were soaked in tap water at 35-40° C. for 10 min. Excess water was removed, and wet integrity measured with a SMS Texture Analyzer and A/TG tensile grips as described in Example 37. Table 18 shows the maximum force before breakage (+1 standard deviation from mean for 3 to 6 samples tested) for the 16 different gelled dried foams.

When foam pieces were placed in tap water, they swelled relatively quickly with observable differences in the hydration rate, both between the batches and within one batch. The foams with the largest pores and the longest gelling time swelled fastest. The thickness of a rehydrated Merck foam was 6.0 mm for the foam kept 60 min on the laboratory bench before drying, and 5.5 mm for the foam kept 0 min on the laboratory bench. The foam prepared with Eskal 500 and kept 0 min on the laboratory bench was not fully hydrated after 30 min and was 4.5 mm thick. The dried gelled foams made with the Merck and Eskal 20 were difficult to handle after rehydration because they were very weak.

TABLE 18

Wet tensile strength of foams with different pore size and gelling rate

| Type of CaCO$_3$ | Wet density, [g/ml] | Gelling time at room temp., [min] | Dry density [g/cm$^3$] | Tensile strength, [g] |
|---|---|---|---|---|
| Merck | 0.20 | 0 | 0.21 | 53 ± 12 |
|  |  | 20 |  | 72 ± 3 |
|  |  | 40 |  | 80 ± 4 |
|  |  | 60 |  | 181 ± 33 |
| Eskal 20 | 0.20 | 0 | 0.21 | 47 ± 7 |
|  |  | 20 |  | 37 ± 8 |
|  |  | 40 |  | 77 ± 8 |
|  |  | 60 |  | 94 ± 3 |
| Eskal 500 | 0.21 | 0 | 0.11 | 311 ± 33 |
|  |  | 20 |  | 409 ± 26 |
|  |  | 40 |  | 375 ± 23 |
|  |  | 60 |  | 411 ± 43 |
| 40% Eskal 20; 60% Merck | 0.19 | 0 | 0.16 | 102 ± 13 |
|  |  | 20 |  | 147 ± 22 |
|  |  | 40 |  | 155 ± 23 |
|  |  | 60 |  | 211 ± 12 |

Having described the invention, we now claim the following and their equivalents.

The invention claimed is:

1. A method for forming a mechanically homogeneous dried gelled foam, the method comprising the steps of:
   a) forming an aqueous dispersion comprising the following ingredients:
      a gel-forming polymer selected from the group consisting of alginates, pectic substances, carrageenans, glycol alginates, and mixtures thereof,
      a gelling agent;
      a water soluble plasticizer;
      optionally, a foaming agent;
      optionally, one or more additives;
      a pH modifier; and
      water;
      in which the gel-forming polymer is dissolved in the water, and the gelling agent is dispersed in the water;
   b) forming a foam from the dispersion, and forming a gelled foam; and
   c) drying the gelled foam to form the dried gelled foam;
   in which the plasticizer comprises more that 50 wt % of the dry gelled foam, exclusive of water and additives and said dried gelled foam is mechanically homogeneous.

2. The method of claim 1 in which the aqueous dispersion comprises the foaming agent.

3. The method of claim 2 in which the foaming agent comprises hydroxy propyl methyl cellulose, methyl cellulose, one or more nonionic surfactants, or a mixture thereof.

4. The method of claim 2 in which the ratio of the plasticizer to the gel-forming polymer in the aqueous dispersion is about 10:1 to about 2:1.

5. The method of claim 4 in which the aqueous dispersion comprises about 0.5 wt % to about 10 wt % of the gel-forming polymer.

6. The method of claim 5 in which the water soluble plasticizer is glycerin, sorbitol, or a mixture thereof.

7. The method of claim 6 in which the gel-forming polymer comprises an alginate or a mixture of alginates.

8. The method of claim 7 in which the amount of gelling agent added is sufficient to saturate from 25% to 200% of the gelling sites of the alginate.

9. The method of claim 8 in which the alginate has a G content of about 40% to about 90% and the alginate has a molecular weight of at least about 150,000 Daltons.

10. The method of claim 5 in which the gelling agent is calcium carbonate.

11. The method of claim 10 in which the pH modifier is glucono delta lactone.

12. The method of claim 11 in which the ratio of the plasticizer to the gel-forming polymer in the aqueous dispersion is about 6:1 to about 4:1, and the aqueous dispersion comprises about 1 wt % to about 6 wt % of the gel-forming polymer.

13. The method of claim 12 in which the foaming agent comprises hydroxy propyl methyl cellulose, methyl cellulose, one or more nonionic surfactants, or a mixture thereof; the water soluble plasticizer is glycerin, sorbitol, or a mixture thereof the gel-forming polymer comprises an alginate or a mixture of alginates; and the amount of gelling agent added is sufficient to saturate from 25% to 200% of the gelling sites of the alginate.

14. The method of claim 1 additionally comprising, after step b) and before step c), the step of adding the foam to a bath of an organic liquid that is miscible with water or in which water is partly soluble that comprises a water soluble plasticizer, and forming foam beads.

15. The method of claim 1 in which the aqueous dispersion is formed by the steps of, in order:
   i) in any order, dissolving the gel-forming polymer, the plasticizer, and, optionally, the foaming agent in water, and dispersing the gelling agent in the water;
   ii) adding the pH modifier to the water;
   in which the foam is formed immediately after step i), or immediately after step ii).

16. The method of claim 15 in which the foaming agent is present and comprises hydroxy propyl methyl cellulose, methyl cellulose, one or more nonionic surfactants, or a mixture thereof the water soluble plasticizer is glycerin, sorbitol, or a mixture thereof the gel-forming polymer comprises an alginate or a mixture of alginates; the amount of gelling agent added is sufficient to saturate from 25% to 200% of the gelling sites of the alginate; the gelling agent is calcium carbonate; the pH modifier is glucono delta lactone; the ratio of the plasticizer to the gel-forming polymer in the aqueous dispersion is about 6:1 to about 4:1, and the aqueous dispersion comprises about 1 wt % to about 6 wt % of the gel-forming polymer.

17. The method of claim 1 in which the additive is present in the aqueous dispersion.

18. The method of claim 17 in which the additive is food.

19. The method of claim 17 in which the additive is a beneficial agent or a mixture of beneficial agents.

20. The method of claim 17 in which the additive is an abrasive.

21. The method of claim 17 in which the additive is a water soluble silver salt.

22. The method of claim 1 additionally comprising, after step c), the step of adding an additive to the dried gelled foam.

23. A dried gelled foam produced by the method of claim 1.

24. A dried gelled foam produced by the method of claim 3.

25. A dried gelled foam produced by the method of claim 13.

26. A dried gelled foam produced by the method of claim 16.

27. The method of claim 1, wherein said gel forming polymer comprises alginate; and said dried gelled foam further comprises a foaming agent comprising at least one of methyl cellulose, hydroxy propyl methyl cellulose, hydroxy propyl cellulose, hydroxy ethyl cellulose and glycol alginate.

28. The method of claim 1, wherein said pH modifier comprises at least one of an anhydride, ester, amide, lactone and lactam.

29. The method of claim 28, wherein said pH modifier comprises at least one of lactic acid lactone, glycolic acid lactone and glucono delta lactone.

30. The method of claim 1, wherein said dried gelled foam has a weight density of 0.04 to 0.09 g/ml.

31. The method of claim 29, wherein said gelling agent comprises at least one of bicarbonates, carbonates, phosphates and tricalcium citrate.

* * * * *